United States Patent
Ravid et al.

(10) Patent No.: US 7,840,375 B2
(45) Date of Patent: Nov. 23, 2010

(54) METHODS AND APPARATUS FOR GENERATING A LIBRARY OF SPECTRA

(75) Inventors: Abraham Ravid, Cupertino, CA (US); Boguslaw A. Swedek, Cupertino, CA (US); Dominic J. Benvegnu, La Honda, CA (US); Jeffrey Drue David, San Jose, CA (US); Jun Qian, Sunnyvale, CA (US); Sidney P. Huey, Fremont, CA (US); Ingemar Carlsson, Milpitas, CA (US); Lakshmanan Karuppiah, San Jose, CA (US); Harry Q. Lee, Los Altos, CA (US)

(73) Assignee: Applied Materials, Inc., Santa Clara, CA (US)

( * ) Notice: Subject to any disclaimer, the term of this patent is extended or adjusted under 35 U.S.C. 154(b) by 153 days.

(21) Appl. No.: 12/059,435

(22) Filed: Mar. 31, 2008

(65) Prior Publication Data

US 2008/0243433 A1 Oct. 2, 2008

Related U.S. Application Data

(60) Provisional application No. 60/949,498, filed on Jul. 12, 2007, provisional application No. 60/909,639, filed on Apr. 2, 2007.

(51) Int. Cl.
*G01B 5/00* (2006.01)
*G06F 19/00* (2006.01)
(52) U.S. Cl. .................................................. 702/172
(58) Field of Classification Search .............. 702/172, 702/33, 40, 76, 170; 700/52, 121
See application file for complete search history.

(56) References Cited

U.S. PATENT DOCUMENTS

| 5,365,340 | A | * | 11/1994 | Ledger ........................ 356/504 |
| 5,436,725 | A | * | 7/1995 | Ledger ........................ 356/504 |
| 5,893,796 | A | | 4/1999 | Birang et al. |
| 5,900,633 | A | | 5/1999 | Solomon et al. |
| 6,093,081 | A | * | 7/2000 | Nyui et al. ....................... 451/6 |
| 6,108,091 | A | | 8/2000 | Pecen et al. |
| 6,153,116 | A | | 11/2000 | Yang et al. |
| 6,172,756 | B1 | | 1/2001 | Chalmers et al. |

(Continued)

FOREIGN PATENT DOCUMENTS

EP 0660076 6/1995

(Continued)

OTHER PUBLICATIONS

U.S. Appl. No. 11/611,640, Ravid et al.

(Continued)

*Primary Examiner*—Michael P Nghiem
*Assistant Examiner*—Cindy H Khuu
(74) *Attorney, Agent, or Firm*—Fish & Richardson

(57) ABSTRACT

A method of generating a library from a reference substrate for use in processing product wafers is described. The method includes measuring substrate characteristics at a plurality of well-defined points of a reference substrate, measuring spectra at plurality of measurement points of the reference substrate, there being more measurement points than well-defined points, and associating measured spectra with measured substrate characteristics.

23 Claims, 15 Drawing Sheets

U.S. PATENT DOCUMENTS

| | | | |
|---|---|---|---|
| 6,184,985 B1 | 2/2001 | Chalmers et al. | |
| 6,190,234 B1 | 2/2001 | Swedek et al. | |
| 6,204,922 B1 | 3/2001 | Chalmers | |
| 6,270,622 B1 * | 8/2001 | Klippert et al. | 156/345.12 |
| 6,271,047 B1 | 8/2001 | Ushio et al. | |
| 6,296,548 B1 | 10/2001 | Wiswesser et al. | |
| 6,361,646 B1 | 3/2002 | Bibby, Jr. et al. | |
| 6,447,370 B1 | 9/2002 | Weldon | |
| 6,573,999 B1 | 6/2003 | Yang | |
| 6,618,130 B2 | 9/2003 | Chen | |
| 6,623,991 B2 | 9/2003 | Johnson et al. | |
| 6,670,200 B2 | 12/2003 | Ushio et al. | |
| 6,676,482 B2 | 1/2004 | Bibby, Jr. et al. | |
| 6,678,046 B2 | 1/2004 | Opsal | |
| 6,678,055 B2 | 1/2004 | Du-Nour et al. | |
| 6,679,756 B2 | 1/2004 | Ishikawa et al. | |
| 6,762,838 B2 | 7/2004 | DuNour | |
| 6,768,967 B2 | 7/2004 | Johnson et al. | |
| 6,801,321 B1 | 10/2004 | Du-Nour | |
| 6,806,105 B2 | 10/2004 | Johnson et al. | |
| 6,806,948 B2 | 10/2004 | Katz et al. | |
| 6,813,034 B2 | 11/2004 | Rosencwaig et al. | |
| 6,819,426 B2 | 11/2004 | Sezginer et al. | |
| 6,836,328 B2 | 12/2004 | Opsal | |
| 6,842,259 B2 | 1/2005 | Rosencwaig et al. | |
| 6,885,467 B2 | 4/2005 | Du-Nour et al. | |
| 6,898,596 B2 | 5/2005 | Aikens et al. | |
| 6,908,374 B2 | 6/2005 | Wang et al. | |
| 6,912,056 B2 | 6/2005 | Hyun et al. | |
| 6,942,546 B2 | 9/2005 | Desai et al. | |
| 6,947,135 B2 | 9/2005 | Johnson | |
| 6,963,407 B2 | 11/2005 | Abe et al. | |
| 6,995,842 B2 | 2/2006 | Opsal | |
| 7,057,744 B2 | 6/2006 | Nomoto et al. | |
| 7,119,908 B2 | 10/2006 | Nomoto et al. | |
| 7,120,553 B2 | 10/2006 | Benvegnu | |
| 7,300,332 B2 | 11/2007 | Kobayashi et al. | |
| 7,324,210 B2 | 1/2008 | De Groot et al. | |
| 7,375,828 B1 | 5/2008 | Aoyagi et al. | |
| 7,460,237 B1 * | 12/2008 | Cramer | 356/445 |
| 7,487,053 B2 * | 2/2009 | Funk et al. | 702/66 |
| 7,614,933 B2 | 11/2009 | Benvegnu et al. | |
| 2002/0005957 A1 * | 1/2002 | Finarov et al. | 356/630 |
| 2002/0030826 A1 * | 3/2002 | Chalmers et al. | 356/630 |
| 2003/0210408 A1 | 11/2003 | Jun et al. | |
| 2004/0042017 A1 | 3/2004 | Cohen et al. | |
| 2004/0080757 A1 * | 4/2004 | Stanke et al. | 356/601 |
| 2004/0087041 A1 * | 5/2004 | Perry et al. | 438/5 |
| 2004/0263868 A1 | 12/2004 | Isei et al. | |
| 2005/0037615 A1 | 2/2005 | Cabib et al. | |
| 2005/0148104 A1 * | 7/2005 | Kota et al. | 438/14 |
| 2006/0020419 A1 * | 1/2006 | Benvegnu | 702/172 |
| 2007/0042681 A1 * | 2/2007 | Benvegnu et al. | 451/6 |
| 2007/0252963 A1 * | 11/2007 | Modderman et al. | 355/53 |
| 2008/0146120 A1 * | 6/2008 | Ravid et al. | 451/6 |
| 2009/0033942 A1 * | 2/2009 | Ravid et al. | 356/448 |

FOREIGN PATENT DOCUMENTS

| | | |
|---|---|---|
| EP | 1176631 | 1/2002 |
| JP | 2000-183001 | 6/2000 |
| JP | 2000-310512 | 11/2000 |
| JP | 2001-287159 | 10/2001 |
| JP | 2002-359217 | 12/2002 |
| JP | 2005-159203 | 6/2005 |
| WO | WO 00/54935 | 9/2000 |
| WO | WO 01/72470 | 10/2001 |
| WO | WO 2004/035265 | 4/2004 |

OTHER PUBLICATIONS

U.S. Appl. No. 12/059,464, Ravid et al.

* cited by examiner

| Wafer Characteristic | Coordinates |
|---|---|
| $T_1$ | $(Xw_1, Yw_1)$ |
| $T_2$ | $(Xw_2, Yw_2)$ |
| ⋮ | ⋮ |
| $T_{m-1}$ | $(Xw_{m-1}, Yw_{m-1})$ |
| $T_m$ | $(Xw_m, Yw_m)$ |

FIG. 5

| Spectrum | Coordinates |
|---|---|
| $S_1$ | $(Xm_1, Ym_1)$ |
| $S_2$ | $(Xm, Ym_2)$ |
| • | • |
| • | • |
| $S_8$ | $(Xm_8, Ym_8)$ |
| $S_9$ | $(Xm_9, Ym_9)$ |
| • | • |
| • | • |
| $S_{n-1}$ | $(Xm_{n-1}, Ym_{n-1})$ |
| $S_n$ | $(Xm_n, Ym_n)$ |

FIG. 7

| Spectrum | Wafer Characteristic |
|---|---|
| $S_1$ | $T_1$ |
| $S_2$ | $T_2$ |
| • | • |
| • | • |
| $S_8$ | $T_2$ |
| $S_9$ | $T_2$ |
| • | • |
| • | • |
| $S_{m-1}$ | ? |
| $S_m$ | ? |

FIG. 8

METHODS AND APPARATUS FOR GENERATING A LIBRARY OF SPECTRA

CROSS-REFERENCE TO RELATED APPLICATIONS

Under 35 U.S.C. §119(e)(1), this application claims the benefit of prior U.S. Provisional Application 60/949,498, filed Jul. 12, 2007, and U.S. Provisional Application 60/909,639, filed Apr. 2, 2007.

TECHNICAL FIELD

This invention relates to metrology, and in one aspect to optical monitoring of substrates during a chemical mechanical polishing process.

BACKGROUND

An integrated circuit is typically formed on a substrate by the sequential deposition of conductive, semiconductive, or insulative layers on a silicon wafer. One fabrication step involves depositing a filler layer over a non-planar surface and planarizing the filler layer. For certain applications, the filler layer is planarized until the top surface of a patterned layer is exposed. A conductive filler layer, for example, can be deposited on a patterned insulative layer to fill the trenches or holes in the insulative layer. After planarization, the portions of the conductive layer remaining between the raised pattern of the insulative layer form vias, plugs, and lines that provide conductive paths between thin film circuits on the substrate. For other applications, such as oxide polishing, the filler layer is planarized until a predetermined thickness is left over the non planar surface. In addition, planarization of the substrate surface is usually required for photolithography.

Chemical mechanical polishing (CMP) is one accepted method of planarization. This planarization method typically requires that the substrate be mounted on a carrier or polishing head. The exposed surface of the substrate is placed against a rotating polishing pad. The polishing pad may be either a "standard" pad or a fixed-abrasive pad. The carrier head provides a controllable load, i.e., pressure, on the substrate to push it against the polishing pad. A polishing liquid, such as a slurry with abrasive particles, is supplied to the surface of the polishing pad.

In order to determine the effectiveness of a polishing operation, a "blank" substrate (e.g., a wafer with multiple layers but no pattern) or a test substrate (e.g., a wafer with the pattern to be used for device wafers) is polished in a tool/process qualification step. After polishing, the substrate is removed from the polishing system and the remaining layer thickness (or another substrate property relevant to circuit operation, such as conductivity) is measured at several points on the substrate surface using an in-line or stand-alone metrology station. The variation in layer thickness provide a measure of the wafer surface uniformity, and a measure of the relative polishing rates in different regions of the substrate. The in-line or stand-alone metrology station can provide extremely accurate and reliable thickness measurements (e.g., using ellipsometry) and precise positioning of a sensor to desired measurement locations on the substrate. However, this metrology process can be time-consuming, and the metrology equipment can be costly.

One problem in CMP is determining whether the polishing process is complete (i.e., whether a substrate layer has been planarized to a desired flatness or thickness). Variations in the initial thickness of the substrate layer, the slurry composition, the polishing pad condition, the relative speed between the polishing pad and the substrate, and the load on the substrate can cause variations in the material removal rate. These variations cause variations in the time needed to reach the polishing endpoint. Therefore, for some applications, determining the polishing endpoint merely as a function of polishing time can lead to unacceptable variations in the post-polishing thickness of the substrate layer. However, removal of the substrate from the polishing apparatus for transportation to an in-line or stand-alone metrology station can lead to an unacceptable reduction in throughput.

Several methods have been developed for in-situ polishing endpoint detection. One class of methods involve optically monitoring the substrate during polishing, e.g., using an optical sensor positioned in the platen that directs a light beam through a window onto the substrate. However, measurements using such an in-situ system usually cannot be precisely positioned at a desired measurement location due to the motion of the substrate relative to the sensor, and the measurements can be less accurate due to noise generated by the polishing environment (e.g., absorption of light by slurry), the limited time available for measurements, and the need for real-time processing of the sensor data.

SUMMARY

This invention relates to a method of generating a library from a reference substrate for use in processing product wafers. The method includes measuring substrate characteristics a plurality of well-defined points of a reference substrate, measuring spectra at plurality of measurement points of the reference substrate, there being more measurement points than well-defined points, and associating measured spectra with measured substrate characteristics.

Implementations of the invention may include one or more of the following. Coordinates of the well-defined points and coordinates of the measurement points may be stored. Associating measured spectra with measured substrate characteristics can include comparing coordinates of the well-defined points with coordinates of the measurement points. Comparing coordinates of the well-defined points with coordinates of the measurement points can include determining a distance a spectra and a well-defined point.

Associating measured spectra with measured substrate characteristics can include determining a well-defined point that is nearest to a particular measurement point, and associating the substrate characteristic of the determined well-defined point with the spectra of the particular measurement point. The substrate characteristic can include a layer thickness, such as a pre- or post-polish layer thickness. Identical spectra exhibiting different layer thickness values can be removed. The plurality of well-defined points can be at substantially similar relative locations within different dies on the reference substrate. At least some of the measurement points are spatially different than the well-defined points. The substrate characteristics can be measured prior to or after measuring the spectra. Measuring the spectra can include scanning a sensor across the reference substrate. A method of monitoring a substrate can include generating a library from a reference substrate according to the method above, scanning a product substrate with a optical monitoring system to generate a plurality of spectra, and determining substrate characteristics for the product substrate based on the library. Scanning the product substrate can include scanning with an in-situ monitoring system or scanning with an in-line monitoring system.

In another aspect, a method of generating a library for use in processing product wafers includes measuring a substrate layer thickness at a first well-defined point and a second well-defined point of a reference substrate, measuring a spectra at a first measurement point of the reference substrate, determining the closer of the first well-defined point and the second well-defined point to the first measurement point, and associating the spectra with the substrate layer thickness of the closer well-defined point.

In another aspect, a computer program product, tangibly stored on machine readable medium, includes instructions operable to cause a processor to perform or cause the steps of the various methods above.

In another aspect, a substrate processing system includes a processing module to process a substrate, a factory interface module configured to accommodate at least one cassette for holding the substrate, a spectrographic monitoring system positioned in or adjoining the factory interface module, and a substrate handler to transfer the substrate between the at least one cassette, the spectrographic monitoring system and the processing module.

Implementations of the invention may include one or more of the following. The spectrographic monitoring system include may an optical probe and may be configured to measure spectra at a plurality of positions on the substrate while the substrate is moving relative to the optical probe. The substrate may be moved by the substrate handler and the optical probe may remain stationary. Spectra may be measured in a plurality of positions that span a diameter of the substrate in less than ten seconds. The plurality of positions may form a non-linear path on the substrate, e.g., a figure-eight path. The spectrographic monitoring system may include an optical probe and may be configured to measure spectra at a plurality of positions on the substrate without aligning the optical probe to well-defined locations on the substrate. The spectrographic monitoring system may be positioned in the factory interface module. A notch alignment system may position a notch of the substrate in a determined orientation.

As used in the instant specification, the term substrate can include, for example, a product substrate (e.g., which includes multiple memory or processor dies), a test substrate, a bare substrate, and a gating substrate. The substrate can be at various stages of integrated circuit fabrication, e.g., the substrate can be a bare wafer, or it can include one or more deposited and/or patterned layers. The term substrate can include circular disks and rectangular sheets.

Possible advantages of implementations of the invention can include one or more of the following. A library of spectra can be assembled, and the spectra can be associated with physical properties of the substrate. Spectra-based endpoint determination can be made in-situ with greater speed and accuracy, and variations in the post-polishing thickness of the substrate layer can be reduced. Spectra-based measurements of substrate characteristics can be made by in-line monitoring systems with great speed.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 illustrates a data structure associating a substrate characteristic with a coordinate for each well-defined points.

FIG. 7 illustrates a data structure associating a spectrum with a coordinate for each measurement point.

FIG. 8 illustrates a library with a data structure associating spectra with substrate characteristics.

Like reference symbols in the various drawings indicate like elements.

DETAILED DESCRIPTION

Figure 1:
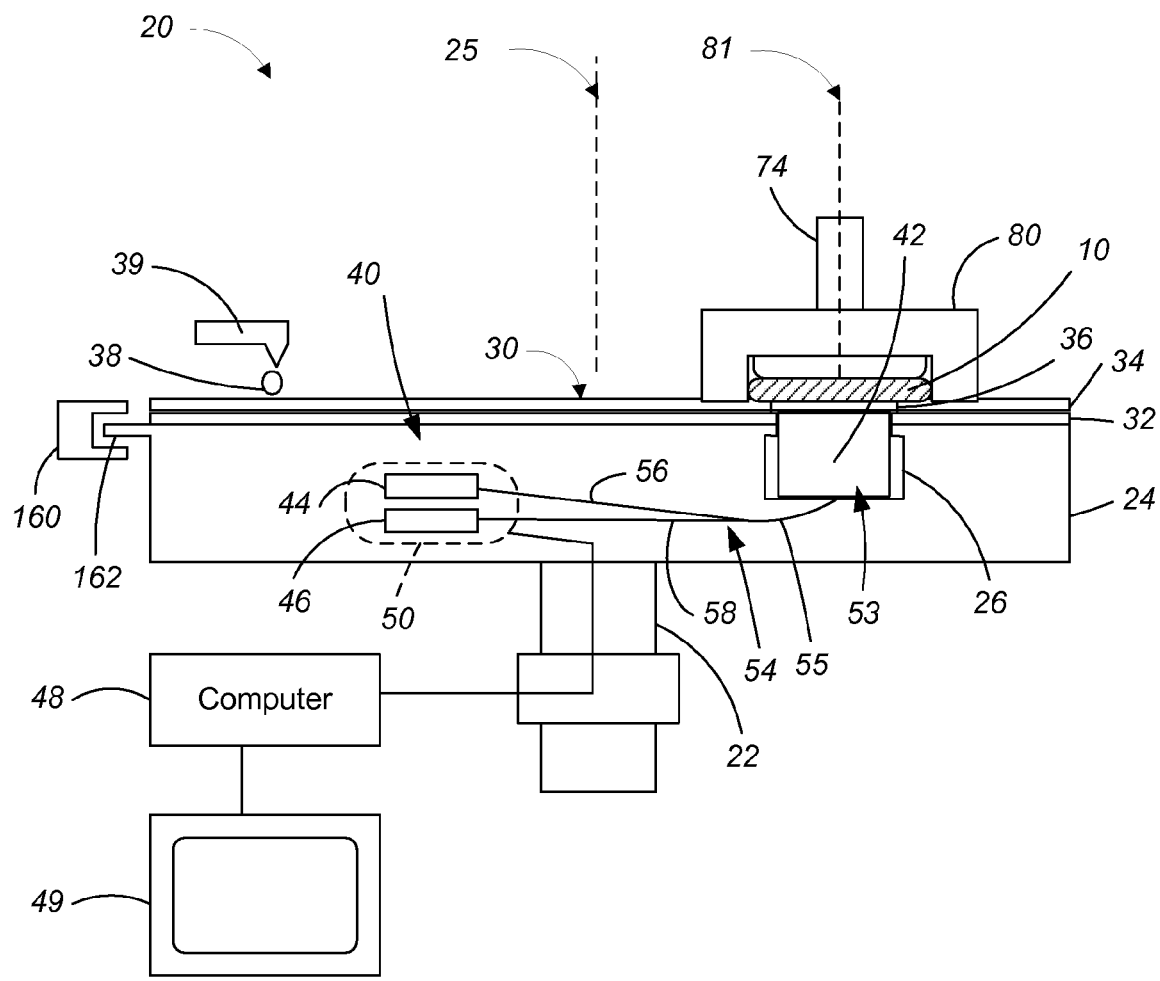
FIG. 1 is a cross-sectional side view of an exemplary chemical mechanical polishing apparatus having an in-situ optical monitoring system.

Referring to FIG. 1, one or more substrates 10 will be polished at a polishing station of a chemical mechanical polishing (CMP) apparatus 20. A description of a polishing apparatus can be found in U.S. Pat. No. 5,738,574, the entire disclosure of which is incorporated herein by reference.

The polishing station includes a rotatable platen 24 on which is placed a polishing pad 30. The platen 24 can be connected to a platen drive motor (not shown). For most polishing processes, the platen drive motor rotates platen 24 at thirty to two hundred revolutions per minute, although lower or higher rotational speeds may be used. The polishing station can also include a pad conditioner apparatus to maintain the condition of the polishing pad.

Polishing pad 30 typically has a backing layer 32 which abuts the surface of platen 24 and a covering layer 34 which is used to polish the wafer 10. Covering layer 34 is typically harder than backing layer 32. However, some pads have only a covering layer and no backing layer. Covering layer 34 can be composed of a polyurethane with pores, e.g., a foamed polyurethane or cast polyurethane with microspheres, and a grooved surface. Backing layer 32 can be composed of compressed felt fibers leached with urethane. A two-layer polishing pad, with the covering layer composed of IC-1000 and the backing layer composed of SUBA-4, is available from Rodel, Inc., of Newark, Del. (IC-1000 and SUBA-4 are product names of Rodel, Inc.).

A carrier head 80 can be supported by a rotatable multi-head carousel. Generally, the carrier head holds the wafer against the polishing pad, distributes a downward pressure across the back surface of the wafer, transfers torque from the drive shaft to the wafer, and ensures that the wafer does not slip out from beneath the carrier head during polishing operations. A description of a carrier head can be found in U.S. Patent Publication No. 2006-0154580, the entire disclosure of which is incorporated herein by reference. In addition, the carrier head 80 can be configured to laterally oscillate across the polishing pad, e.g., move along a radius of the polishing pad.

A polishing liquid, e.g., a slurry 38 containing abrasive particles, can be supplied to the surface of polishing pad 30 by a slurry supply port or combined slurry/rinse arm 39.

In typical operation, the platen is rotated about its central axis 25, and the carrier head 80 is rotated about its central axis 81 and translated laterally across the surface of the polishing pad.

The polishing apparatus 20 also includes an in-situ optical monitoring system 40, which can be used to determine a polishing endpoint of the wafer being polished, as will be discussed below. The optical monitoring system includes a light source 44 and a light detector 46. Light passes from the light source 44, through an optical access 36 in the polishing pad 30, impinges and is reflected from the substrate 10 back through the optical access 36, and travels to the light detector 46.

The optical access 36 through the polishing pad 30 to the substrate can be provided by an aperture in the pad or a solid window. The solid window can be secured to the polishing pad, although in some implementations the solid window can be supported on the platen 24 and project into an aperture in the polishing pad. If the optical access 36 is in the form of a solid window, the solid window can include, for example, a rigid crystalline or glassy material (e.g., quartz or glass), a softer plastic material (e.g., silicone, polyurethane or a halogenated polymer such as a fluoropolymer), or a combination of these materials. The solid window can be transparent to white light or light(s) at other wavelengths.

A bifurcated optical cable 54 can be used to transmit the light from the light source 44 to the optical access 36 and back from the optical access 36 to the light detector 46. The bifurcated optical cable 54 can include a "trunk" 55 and two "branches" 56 and 58.

The in-situ optical monitoring system 40 can include an optical assembly 53 that is removably secured to the platen 24 in a recess 26 in the platen 24 so that the optical assembly 53 rotates with the platen 24. The optical access 36 can be aligned with the recess 26 and the optical assembly 53. The recess 26 and the optical access 36 can be positioned such that they have a view of the substrate 10 during a portion of the platen's rotation, regardless of the translational position of the carrier head. The optical assembly 53 can hold one end of the trunk 55 of the bifurcated fiber optic cable 54, which is configured to convey light to and from a substrate surface being polished. The optical head 53 can include one or more lenses to focus or collimate the light beam. The optical head 53 can also include a window overlying the end of the bifurcated fiber optic cable 54. Alternatively, the optical assembly 53 can merely hold the end of the trunk 55 adjacent the solid window in the polishing pad. A refractive index gel can be applied to a bottom surface of the window so as to provide a medium for light to travel from the truck of the fiber optic cable to the window.

The in-situ optical monitoring system 40 can also include an in-situ monitoring module 50 that is removably secured to the platen 24. The in-situ monitoring module 50 can include one or more of the following: the light source 44, the light detector 46, and circuitry for sending and receiving signals to and from the light source 44 and light detector 46. For example, the output of the detector 46 can be a digital electronic signal that passes through a rotary coupler, e.g., a slip ring, in the drive shaft 22 to the controller for the optical monitoring system. Similarly, the light source can be turned on or off in response to control commands in digital electronic signals that pass from the controller through the rotary coupler to the module 50.

The in-situ monitoring module can also hold the respective ends of the branch portions 56 and 58 of the bifurcated optical fiber 54. The light source 44 is operable to transmit light, which is conveyed through the branch 56 and out the end of the trunk 55 located in the optical head 53, and which impinges on a substrate being polished. Light reflected from the substrate is received at the end of the trunk 55 located in the optical head 53 and conveyed through the branch 58 to the light detector 46.

In one implementation, the bifurcated fiber cable 54 is a bundle of optical fibers. The bundle includes a first group of optical fibers and a second group of optical fibers. An optical fiber in the first group is connected to convey light from the light source 44 to a substrate surface being polished. An optical fiber in the second group is connected to received light reflecting from the substrate surface being polished and convey the received light to a light detector. The optical fibers can be arranged so that the optical fibers in the second group form an X-like shape that is centered on the longitudinal axis of the bifurcated optical fiber 54 (as viewed in a cross section of the bifurcated fiber cable 54). Alternatively, other arrangements can be implemented. For example, the optical fibers in the second group can form V-like shapes that are mirror images of each other. A suitable bifurcated optical fiber is available from Verity Instruments, Inc. of Carrollton, Tex.

There is usually an optimal distance between the polishing pad window and the end of the trunk 55 of bifurcated fiber cable 54 proximate to the polishing pad window. The distance can be empirically determined and is affected by, for example, the reflectivity of the window, the shape of the light beam emitted from the bifurcated fiber cable, and the distance to the substrate being monitored. In one implementation, the bifurcated fiber cable is situated so that the end proximate to the window is as close as possible to the bottom of the window without actually touching the window. With this implementation, the polishing apparatus 20 can include a mechanism, e.g., as part of the optical assembly 53, that is operable to adjust the distance between the end of the bifurcated fiber cable 54 and the bottom surface of the polishing pad window. Alternatively, the proximate end of the bifurcated fiber cable is embedded in the window.

The light source 44 is operable to emit a broad wavelength band of light, e.g., white light. In some implementations, the white light emitted includes light having wavelengths of 200-800 nanometers. A suitable light source is a xenon lamp or a xenon-mercury lamp. In some implementations, the light source generates infrared or ultraviolet light.

The light detector 46 can be a spectrometer. A spectrometer is basically an optical instrument for measuring properties of light, for example, intensity, over a portion of the electromagnetic spectrum. A suitable spectrometer is a grating spectrometer. Typical output for a spectrometer is the intensity of the light as a function of wavelength.

Optionally, the in-situ monitoring module 50 and optical assembly 53 can include additional other sensor elements in addition to the spectrometer, such as an eddy current sensor, a monochromatic interferometric optical sensor, or a friction sensor.

The light source 44 and light detector 46 are connected to a computing device 48 operable to control their operation and to receive their signals. The computing device can include a microprocessor situated near the polishing apparatus, e.g., a programmable computer, such as a personal computer. The computing device can, for example, synchronize activation of the light source 44 with the rotation of the platen 24.

Figure 2:
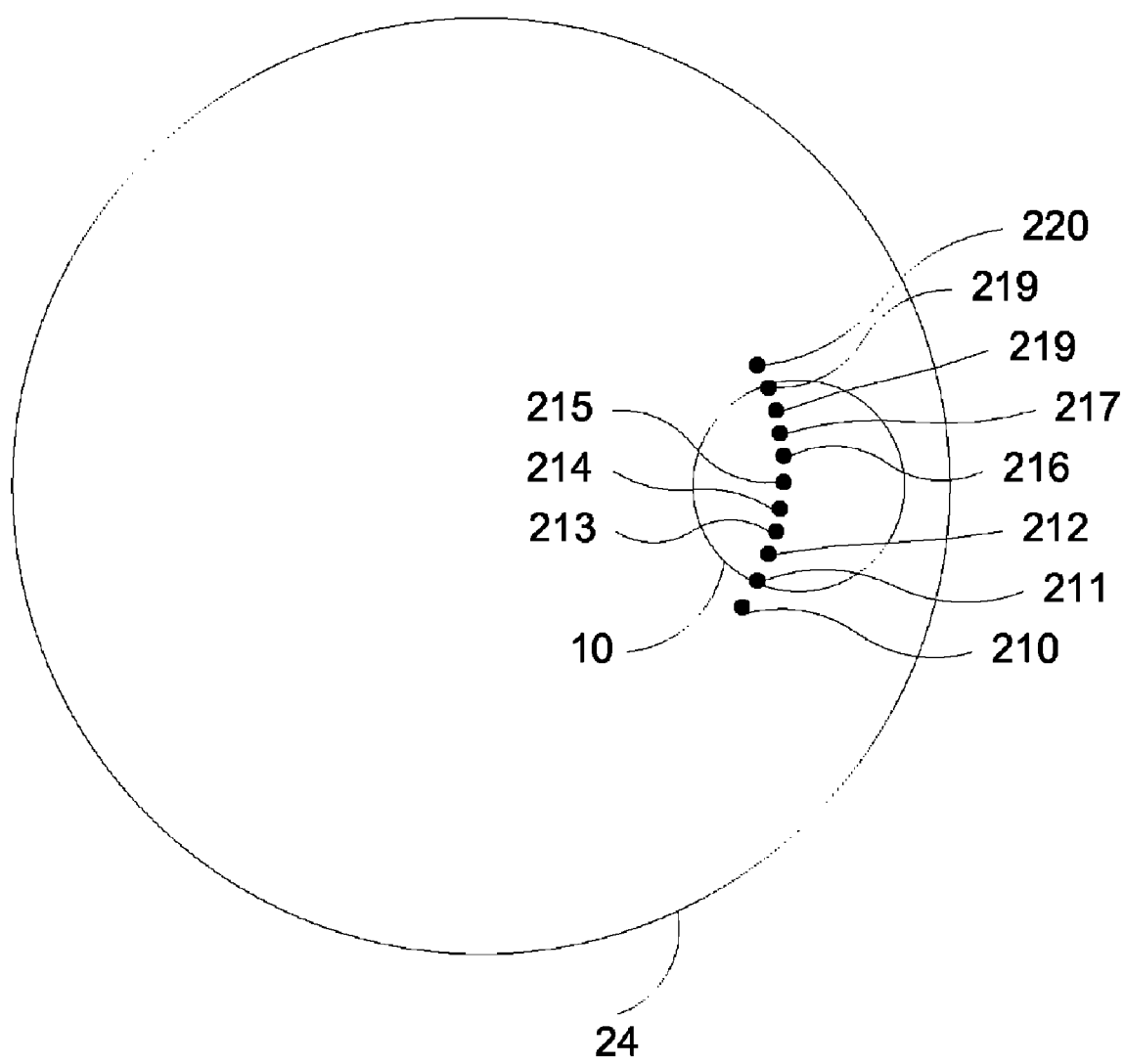
FIG. 2 illustrates an exemplary path of spectra measurements by an in-situ monitoring system across a substrate.

As shown in FIG. 2, the optical monitoring system can make a sequence of spectral measurements as the optical assembly 53 and optical access 36 scan across the substrate. Each of points 201-211 represent a location on the substrate 10 where light from the in-situ monitoring system impinges and reflects off to provide a spectral measurement. As shown in FIG. 2, the locations can trace an arc across the substrate due to the rotation of the platen 24. Optionally, the computer can cause the light source 44 to emit a series of flashes starting just before and ending just after the substrate 10 passes over the optical access 36 module, with each flash corresponding to a measurement location. Alternatively, the computer can cause the light source 44 to emit light continuously starting just before and ending just after the substrate 10 passes over the in-situ monitoring module.

The computing device 48 can be programmed to store spectral intensity measurements from the detector, to display the spectra on an output device, to calculate the remaining thickness, amount removed, and polishing rate from the spectral intensity measurements, and/or to detect the polishing endpoint. The computing device 48 also can be configured to cause, for example, the polishing rate and polishing time of the polishing apparatus to be adjusted based upon the received light.

Generally, in order to calculate a thickness of a layer on the substrate or to detect a polishing endpoint based on the spectrum measured by the optical monitoring system 40, a measured spectrum is compared to a library of reference spectra.

Figure 3:
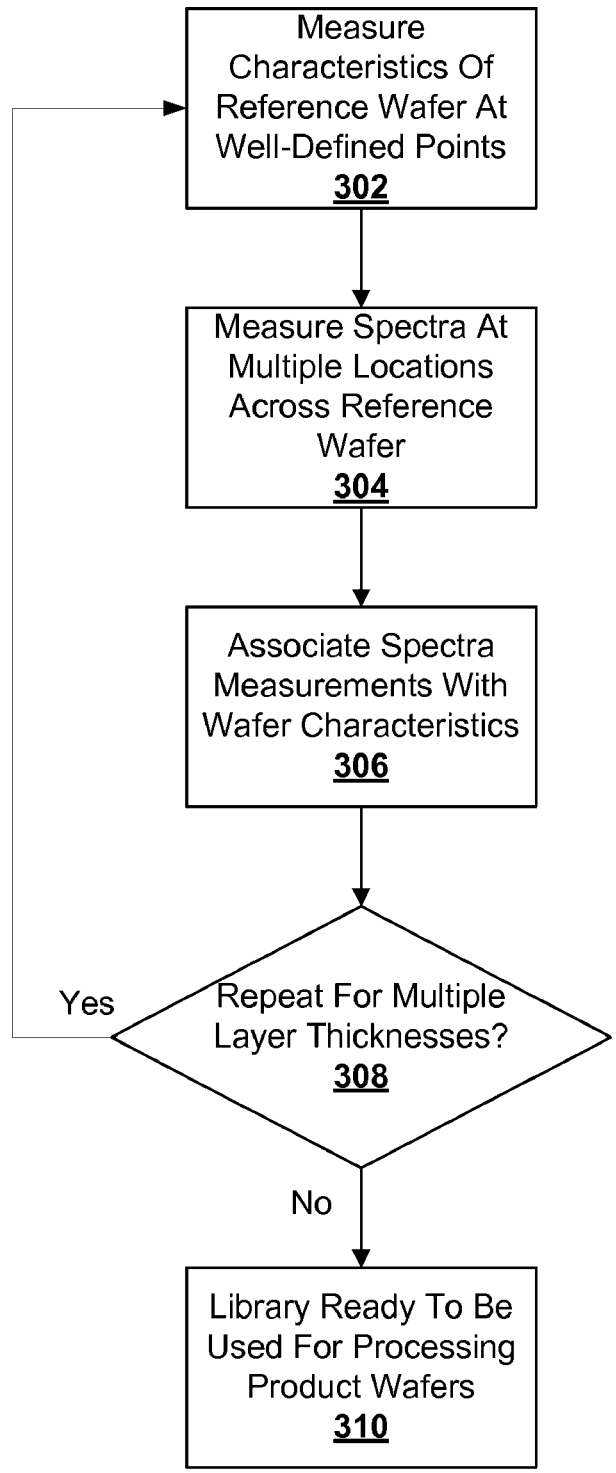
FIG. 3 shows an exemplary process for generating a library that associates substrate characteristics with spectra.

FIG. 3 shows an exemplary process 300 for generating a library that associates reference spectra with substrate characteristics.

Initially, at least one characteristic of a reference substrate, e.g., of a substrate layer, is measured at multiple locations on the reference substrate (step 302). For each location, the measured characteristic and the location of the measurement are stored, e.g., in a first data structure in a computer-readable medium.

The reference substrate should have the same pattern and die feature geometry as an actual product substrate would have at the same point in the manufacturing process, although the reference substrate need not itself be intended to be a product substrate. The characteristic should be measured for at least a substrate that has approximately the thickness as the product substrate will have when measured by a spectrographic system that will use the library. For example, if the product substrate will be measured by an in-line system pre or post-polishing, then the reference substrate should be measured with approximately the expected pre or post-polishing thickness, respectively. If the product substrate will be measured by an in-situ monitoring system, then the reference substrate should be measured for at least the desired post-polishing substrate layer thickness, but as discussed below, the characteristic can be measured for one or more reference substrates at multiple different stages of polishing of the substrate layer.

The characteristic can be a physical property of the substrate that impacts the performance of circuitry on the substrate. An exemplary physical characteristic is a thickness of a film of interest, e.g., the outermost layer undergoing processing. Other thickness-derived characteristics can include step height or erosion. Other possible physical characteristics of the film include conductivity. Alternatively, the characteristic can be a manufacturing metric, e.g., a yield. In addition, the film of interest need not be the outermost layer, e.g., the physical characteristic can be a thickness of an underlying layer.

The substrate characteristics can be measured using a metrology system that provides precise positioning of a sensor to a desired measurement location on the substrate. The metrology system can be part of an in-line or stand-alone metrology station. The metrology station can include positional sensors and alignment mechanism for aligning the substrate and the sensors so that the same location is repeatedly and accurately measured for different substrates. If the metrology system measures substrate layer thickness, it can be a non-contact optical metrology system, such an optical metrology system that uses spectral intensity and/or polarization information to calculate layer thickness, or it can be a contact profilometer. If the metrology system measures substrate layer conductivity, it can include a four-point probe. Suitable optical metrology systems for measuring the substrate layer thickness are available from Nova Measuring Instruments and Nanometrics.

The characteristic is measured at a multiple locations of interest on the reference substrate. In some implementations, these locations are "well-defined" points, i.e., locations at which a metrology device can generate an accurate and reliable measurement without relying on this invention. For example, in the context of a conventional non-contact optical metrology device, a well defined location is a location at which the optical model used by the metrology device can be used to accurately calculate the substrate layer thickness a priori from the measured properties of the reflected light (e.g., spectral intensity and polarization) with a reasonable amount of computational processing power. For example, in the context of a conventional four-point probe, a well defined location is a location with sufficiently large conductive area for placement of the probe. Locations having a lower density of geometrical features than other discrete regions of the wafer can be selected as well-defined points. For example, well-defined points may include regions in which bond pads are placed, or regions in which surfaces of uniform material composition are formed.

The well-defined points can be selected so that each measurement on a particular substrate occurs for locations in different dies but at the same relative position within each die. For a particular substrate at a particular stage of polishing, the number of locations measured can be equal to or less than, e.g., less than, the number of dies on the substrate. The measurement locations can be selected to be generally uniformly spaced across the substrate.

Figure 4:
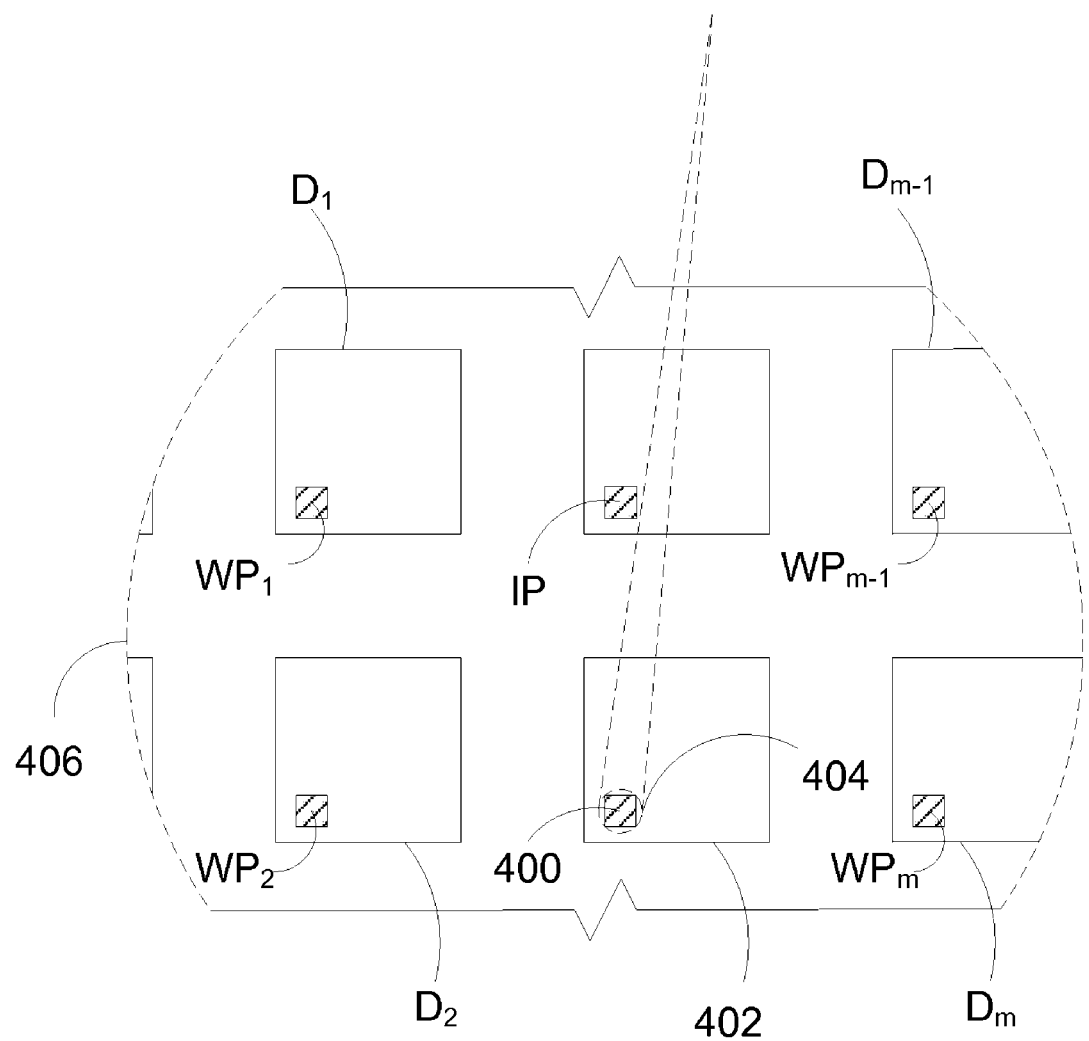
FIG. 4 illustrates a portion of a reference wafer having exemplary well-defined points.

FIG. 4 illustrates a reference wafer having exemplary well-defined points. Referring to FIG. 4, the reference wafer 406 may contain one or more die features 402 (exemplary dies are labeled $D_1, D_2 \ldots D_{m-1}$ and $D_m$). To provide accurate thickness profile analysis of the reference wafer 406, a thickness from each well-defined point 402 (exemplary well-defined points are labeled $WP_1, WP_2 \ldots WP_{m-1}$ and $WP_m$) is measured. Specifically, light is impinged upon each well-defined point, as shown by the measurement spot 404, and portions of the light reflected off the well-defined points 300a-300f are received. Based on spectra detected in the reflected light, thickness measurement at these well-defined points 300a-300f can be obtained.

FIG. 5 illustrates a first data structure generated from collected data that associates the coordinates of at least some of, and possibly each, well-defined point with a corresponding substrate characteristic. Referring to FIGS. 4 and 5, the substrate characteristic, such as thicknesses, of the reference wafer is measured at well-defined points $WP_1, WP_2 \ldots WP_{m-1}$ and $WP_m$ positioned at coordinates $(Xw_1, Yw_1)$, $(Xw_2, Yw_2) \ldots (Xw_{m-1}, Yw_{m-1})$ and $(Xw_m, Yw_m)$, respectively. Of course, a different coordinate system (e.g., R, θ) could be used.

As shown, wafer characteristic $T_1$ is measured for well-defined point $WP_1$ at coordinates $(Xw_1, Yw_1)$. Similarly, wafer characteristics $T_2, \ldots T_{m-1}$ and $T_m$ are measured for well-defined points $WP_2 \ldots WP_{m-1}$ and $WP_m$ at coordinates $(Xw_2, Yw_2), \ldots (Xw_{m-1}, Yw_{m-1})$ and $(Xw_m, Yw_m)$, respectively. These measurements can then be stored in the first data structure. If the substrate characteristics were calculated from measured spectra, then the data structure can optionally also store the measured spectrum associated with each coordinate. In addition, for each measurement or group of measurements, the data structure can store a unique identifier of the reference substrate, and data indicating the stage of polishing of the reference substrate layer (e.g., an elapsed polishing time or a number of platen rotations).

In some implementations, substrate characteristic are calculated for at least some intermediate points. These intermediate points can have the same relative positioning within each die as the well-defined points. The intermediate points can be well-defined points at which the substrate characteristic was not measured, but can also be other points in a die.

The substrate characteristic of the intermediate points can be calculated by linear interpolation or extrapolation from measured well-defined points, particularly the nearest several measured well-defined points, e.g., nearest two to four well-defined points, on the reference substrate. For example, referring to FIG. 4, if substrate layer thicknesses $T_1$ and $T_{m-1}$ are measured for points $WP_1$ and $WP_{m-1}$, and the well-defined and intermediate points are uniformly spaced, then the thickness for intermediate point IP can be calculated as the average of $T_1$ and $T_{m-1}$. More generally, the linear interpolation can be a weighted average of nearby measured well-defined points with weighting based on relative distance to the well-defined points.

Referring back to FIG. 3, at step 304, spectra are measured at multiple locations across the reference substrate. For each location, the spectra and the location of the measurement are stored, e.g., in a data structure in a computer-readable medium.

The spectra are measured for at least some locations (hereinafter "measurement points") other than the well-defined points, although it is permissible for spectra to also be measured at locations that overlap with the well-defined points. However, the measurement points need not selected so that each measurement occurs at the same relative position within a die.

The spectra can be measured with an optical monitoring system that does not provide precise positioning of a sensor to a desired measurement location on the substrate. For example, the spectra can be measured with an optical monitoring system that scans a sensor across the substrate at relatively high speed (e.g., across a 300 mm diameter wafer in less than 10 seconds, e.g, in less than 5 seconds), and without halting. The optical monitoring system can be part of an in-situ monitoring system, e.g., at a polishing station, or an in-line metrology station. The spectra can measured using an optical monitoring system with substantially the same configuration as the in-situ monitoring system to be used at the polishing system (e.g., as described above with reference to FIG. 1). In one implementation, the spectra are measured using the same in-situ optical monitoring system as the one that will be used in the polishing system. In another implementation, the monitoring system can be an in-line or stand alone system that otherwise mimics the in-situ monitoring system, e.g., using the same light source, detector, sampling rate, fiber optic connector and window, but is not in a polishing station.

For a particular substrate at a particular stage of polishing, the number of measurement points can be greater than the number of measured well-defined locations, and can be much greater, e.g., ten or more times greater, e.g., one-hundred or more times greater. At least some dies include more than one measurement point. In general, the spacing between measurement points is less than the spacing between the well-defined locations, and the density of measurement points is also greater than the density of the well-defined locations. The number of measurement points can be greater than the number of dies on the substrate.

For example, referring to FIG. 6, assuming that the spectra are measured using an in-situ optical monitoring system as described with reference to FIG. 1 above, the light beam creates a sweeping path 610 and spectra are measured along the sweeping path, as indicated by the measurement points 612 $MP_1, MP_2 \ldots MP_{m-1}$ and $MP_m$.

The number of measurement points can depend on the sampling rate of the detector 46. The detector 46 can have a sampling rate between about 10 and 100 Hz, corresponding to a sampling period between about 2.5 and 100 milliseconds. Each time the detector 46 is sample, the in-situ optical monitoring system 40 retrieves spectral data, such as intensity and reflectance data, from an associated measurement point 612. The computing device 48 can cause the light source 44 to emit a series of light beam starting just before and ending just after the reference wafer 406 passes over the optical module 53, or the light beam can be on continuously.

Figure 6:
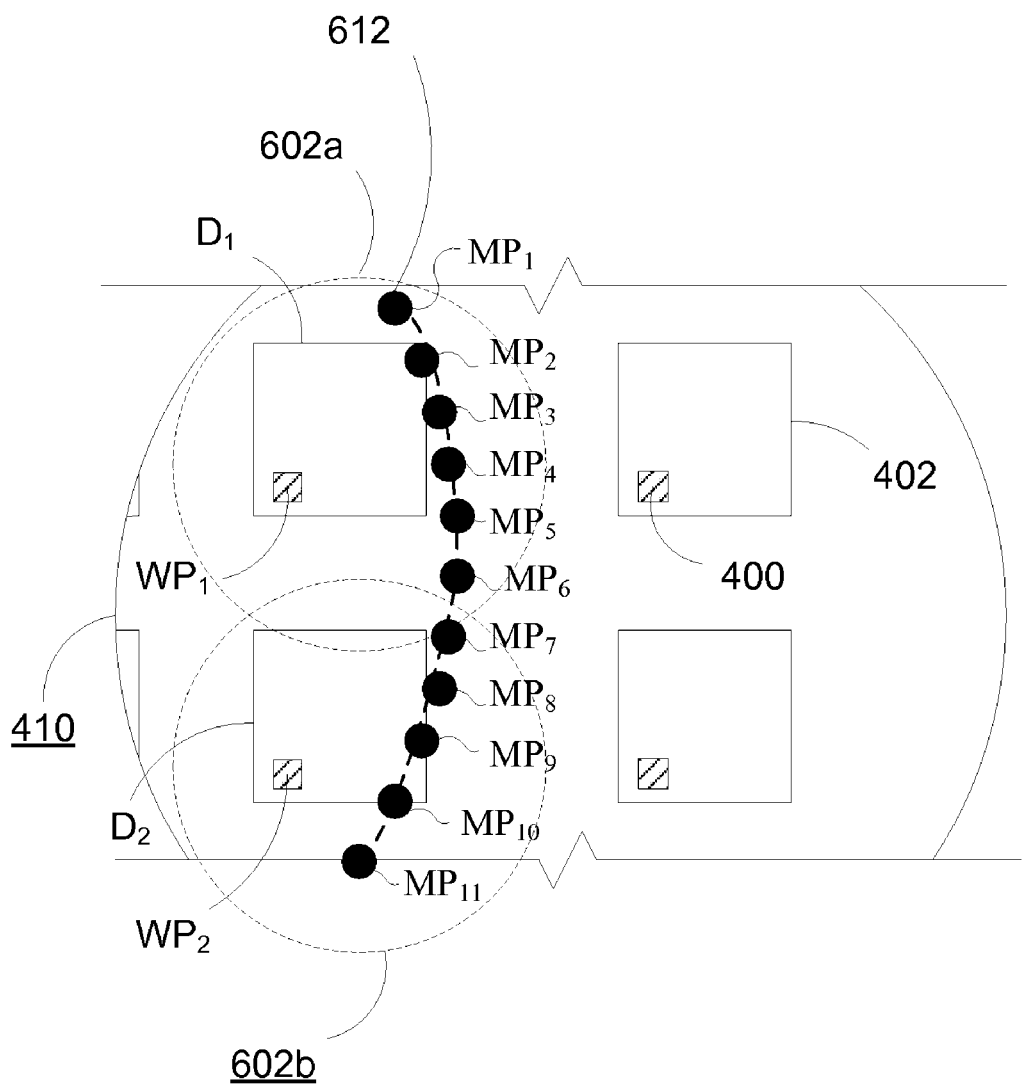
FIG. 6 illustrates a portion of a reference wafer having exemplary measurement points.

Although FIG. 6 shows only eleven measurement points $MP_1, MP_2, \ldots MP_{10}$ and $MP_{11}$, this is illustrative and there could be many more measurement points. The number of measurement points depends on the platen rotation rate and the sampling rate of the detector 46. Of course, a lower triggering rate can result in fewer (and more widely spaced) measurement points, whereas a faster triggering rate can result in a larger number of (and more closely spaced) measurement points. Similarly, a lower rotation rate can result in a larger number of measurement points, whereas a faster rotation rate can result in fewer measurement points.

Also, more than a single sweep can be performed on a particular reference substrate at a particular stage of polishing to produce a measurement points. From the measurement points, the computing device 48 accumulates a set of intensity or reflectance measurements, each associated with a measurement time (e.g., time between a previous sweep and a subsequent sweep).

Spectra from the measurement points 612 can be collected using an optical monitoring tool capable of producing measurement in broad wavelength range, covering, for example, the deep ultraviolet (e.g., wavelengths below 300 nm), ultraviolet, visible or infrared wavelength regions. The wavelength range in which measurement is to be taken can include an entire or a partial segment of the in-situ optical monitoring system's operating wavelength range.

For illustrative purposes, spectra $S_1, S_2, \ldots S_8, S_9 \ldots S_{m-1}$ and $S_m$ are measured at measurement points $MP_1, MP_2 \ldots, MP_8, MP_9 \ldots MP_{m-1}$ and $MP_m$ positioned at coordinates $(Xm_1, Ym_1), (Xm_2, Ym_2) \ldots (Xm_8, Ym_8), (Xm_9, Ym_9) \ldots (Xm_{m-1}, Ym_{m-1})$ and $(Xm_m, Ym_m)$, respectively.

FIG. 7 illustrates a second data structure generated from collected data that associates the coordinates of each measurement point with a corresponding spectrum. As shown, spectra $S_1$ is measured at coordinates $(Xm_1, Ym_1)$. Similarly, spectra $S_2 \ldots S_{m-1}$ and $S_m$ are measured at coordinates $(Xm_2, Ym_2) \ldots (Xm_{n-1}, Ym_{n-1})$ and $(Xm_n, Ym_n)$ respectively. Of course, a different coordinate system (e.g., R, θ) could be used.

The coordinate position of each measurement point at which a spectrum is obtained can be determined by using methods similar to those described in U.S. Pat. Nos. 7,018, 271, 7,097,537, and 7,153,185 the disclosures of which is incorporated herein by reference. In particular, these disclosures describe calculation of a radial positions of a measurement, and an angular position can be calculated from a carrier head angular position at the time of measurement, e.g., as sensed by a rotary encoder. Of course, the R, θ coordinate determination can be transformed into another coordinate system (e.g., X, Y).

In addition, for each measurement or group of measurements, the second data structure can store a unique identifier of the reference substrate, and data indicating the stage of polishing of the reference substrate layer (e.g., an elapsed polishing time or a number of platen rotations).

Returning to FIG. 2, at step 206, spectra measured from measurement points are associated with substrate characteristics based on predetermined conditions. The associated spectra and substrate characteristics are stored to form a library. For example, each spectrum can be linked to a substrate characteristic of a nearby well-defined point based on the coordinates of the measurement point at which the spectrum was measured. Associating spectra with substrate characteristics will be described in further detail below with reference to FIG. 9.

Figure 9:
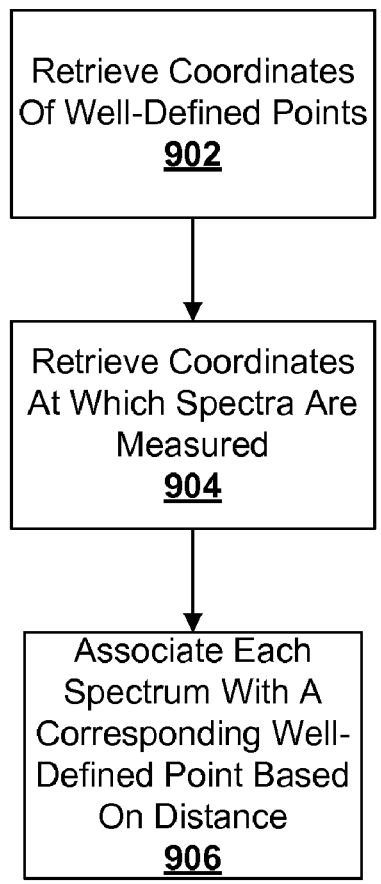
FIG. 9 illustrates an exemplary method for associating spectra with substrate characteristics.

FIG. 9 illustrates an exemplary process 900 for associating spectra with wafer characteristics. A set of well-defined points can be determined for use in generating the library (step 902). Typically, for a particular substrate at a particular stage of polishing, all of the well-defined points at which the substrate characteristic was measured would be used, but it is possible for fewer than all of the well-defined points to be used to generate the library. Similarly, a set of measurement points is determined for use in generating the library (step 904). Again, typically for a particular substrate at a particular stage of polishing, all of the measurement points at which spectra were measured would be used, but it is possible for fewer than all of the measurement points to be used to generate the library.

For each measurement point in the set, one of well-defined points is selected, and the substrate characteristic of the selected well-defined point is assigned to the spectra of the measurement point in the library (step 904). The selected well-defined point is near the measurement point, e.g., one of the four closest measurement points. In one implementation, the well-defined point closest to the measurement point is selected. This can be accomplished by comparing the coordinates of the measurement point to the coordinates of well-defined points and/or calculating distances between the measurement point and the well-defined points. Once the distance between a measurement point and neighboring well-defined points are determined, an association can be established by identifying a well-defined point closest to the measurement point, and linking the spectrum previously measured at that well-defined point to the wafer characteristic(s) associated with the measurement point. In another implementation, the selected well-defined point is the well-defined point in the same die as the measurement point.

As an example, referring to FIG. 6, assuming that coordinates $(Xm_1, Ym_1)$ and $(Xm_2, Ym_2)$ of measurement points $MP_1$ and $MP_2$ are closest to well-defined points $WP_1$ and coordinates $(Xm_8, Ym_8)$ and $(Xm_9, Ym_9)$ of measurement points $MP_8$ and $MP_9$ are closest to well-defined points $WP_2$, then associations between spectra $S_1$ and $S_2$ and wafer characteristic $T_1$, and between spectra $S_8$ and $S_9$ and wafer characteristic $T_2$ are established (see FIG. 8). Of course, associates between the spectra for the other measurement points and substrate characteristics for other well-defined points can also be made.

In some implementations, to expedite the process of distance determination, a predetermined distance or zone from a well-defined point can be identified in advance so that spectra measured at measurement points falling within the predetermined distance or zone are automatically recognized and associated with the wafer characteristics at that well-defined point. For example, still referring to FIG. 6, a spectrum of any measurement point falling inside a first zone 602a is automatically associated with the wafer characteristics of the well-defined point $WP_1$, and spectrum of any measurement point falling inside a second zone 602b is automatically associated with the wafer characteristics of the well-defined point $WP_2$. The definition of the zone for each well-defined point can be stored in the first data structure.

In these implementations, associations for spectra of measurement points falling inside an overlapping region of both the first and second zones can be established by using the distance technique discussed above. For example, measurement point $MP_7$ is situated between the boundaries of the first zone 602a and the second zone 602b. If the distance between the measurement point $MP_7$ and the well-defined point $WP_1$ is shorter than that between the measurement points $MP_7$ and the well-defined point $WP_2$, then the association between the spectrum at the measurement point $MP_7$ and substrate characteristics at the well-defined point $WP_1$ is established. Conversely, if the distance between the measurement point $MP_7$ and the well-defined point $WP_1$ is longer than that between the measurement point $MP_7$ and the well-defined point $WP_2$, then the association between the spectrum at measurement point $MP_7$ and substrate characteristics at the well-defined point $WP_2$ is established.

FIG. 8 illustrates a third data structure generated from collected data that associates spectra with substrate characteristics and that forms the library. As shown, spectrum $S_1$ is associated with thickness $T_1$, spectrum $S_2$ is associated with thickness $T_1$, spectrum $S_8$ is associated with thickness $T_2$ and spectrum $S_9$ is associated with thickness $T_2$. Optionally, information related to the distance between each measurement point and well-defined point, including coordinates thereof, can be stored in the library.

Returning to FIG. 2, at step 208, it is determined whether spectra and substrate characteristic measurements of a reference substrate are needed at additional different polishing stages. If it is determined that measurements are needed at additional different polishing stages ("Yes" branch of step 208), steps 202-206 are repeated. In general, steps 202-206 can be repeated until spectra and substrate characteristics are accumulated for a sufficient number of different thicknesses to ensure reliable operation during polishing of actual product wafers.

In one implementation, the reference substrate is initially measured at a partially polished state. After substrate characteristics and spectra have been measured in, the reference substrate can be transferred back to the polishing apparatus to partially polish an additional incremental amount of substrate layer material. In fact, spectra can be collected during the polishing process (e.g., using the in-situ monitoring system described above to collect spectra from the last platen rotation before polishing is halted). The reference substrate is then removed from the polishing apparatus for measurement of the substrate characteristics at the well-defined locations, e.g., using a conventional in-line or stand-alone metrology system. Of course, the reference substrate can then be sent back to the polishing system for additional polishing.

Otherwise (at "No" branch of step 208), process 200 indicates that the library is prepared to be used for processing actual product wafers (step 210).

Steps 202 and 204 can be performed in the order listed or in reverse of the order listed. Thus, spectra measurement at multiple measurement points across the reference substrate can be performed before or after the measurement of substrate characteristics at well-defined points. In addition, in some implementations, some operations of steps 202-206 can be performed in another order or in parallel to achieve the same result. For example, an association between spectrum measurements and wafer characteristics can be performed as each spectrum is received. As another example, if the substrate characteristics are calculated for some of the well-defined points (e.g., by linear interpolation), the calculation can be performed after the closest well-defined point has been identified for a spectrum.

The library can reside in the memory of the computing device 48. The library can be updated with new data (e.g., if a product substrate is directed to a metrology station, then spectra from the product substrate collected from the in-situ monitoring system, e.g., from the last platen rotation before polishing was halted, could be associated with the substrate characteristics measured at the metrology station). If desired, the library also can include spectra that are not collected but are theoretically generated. Other parameters such as time in which the spectra are measured also can be stored in the library. In addition, the library is not limited to storing data collected from a single substrate, and can include spectra collected from multiple substrates.

Because precise alignment of the measurement tools at the well-defined points is no longer required, the library can significantly increase the overall speed with which substrate characteristics can be determined, and thus the throughput of the polishing apparatus can be increased. To optimize the throughput of the polishing apparatus, a high density of spectra and wafer characteristics covering an entire wafer area are captured before, during and after polishing so that a sufficient number of wafer characteristics and spectra measurements is stored. This enables high speed, high volume, precise real time thickness extraction and reporting. However, if during polishing of an actual product wafer, a measured spectrum is found not to have a matching spectrum stored in the library, the library can be immediately updated to include the measured spectrum and its associated wafer information.

Once a sufficient number of established associations are identified and collected, the library can be used for monitoring during processing of actual product wafers. During actual processing, the optical monitoring system sweeps across a product substrate and measures a sequence of spectra from the reflected light, and the library can be searched for a matching spectra. The search may include direct comparison of the measured spectra to those stored in the library, or using a combination of searching and fitting algorithms. The substrate characteristics associated with the spectra selected from the search can then be used for monitoring or control of the polishing process.

In some implementations, endpoint can be called when a measured spectrum has a desired substrate characteristic. For example, as discussed above, for the spectra measured during polishing, the closest matching spectrum in the library can be identified, e.g., using searching and/or fitting algorithms. If the substrate characteristics, e.g., thickness, of the matching spectrum in the library has the desired characteristic, e.g., a desired thickness, then the polishing endpoint is triggered.

In another implementation, the library is searched in advanced for a desired endpoint criterion, e.g., a desired thickness, and one or more spectra which have a substrate characteristic with the desired criterion are identified as desired spectra. Then, during polishing, for the spectra measured during polishing, the closest matching spectrum in the library can be identified. Polishing can be halted when the measured spectrum matches a desired spectra from the library.

In some implementations, the library is not used for endpoint determination, but is merely used for monitoring and/or feedback control of pressure applied by the carrier head to the substrate. For example, endpoint could be detected using a difference traces between the current spectra measured during polishing and a reference spectrum, as described in U.S. Patent Application Publication No. 2007/0042675, the disclosure of which is incorporated herein by reference in its entirety.

Figure 10:
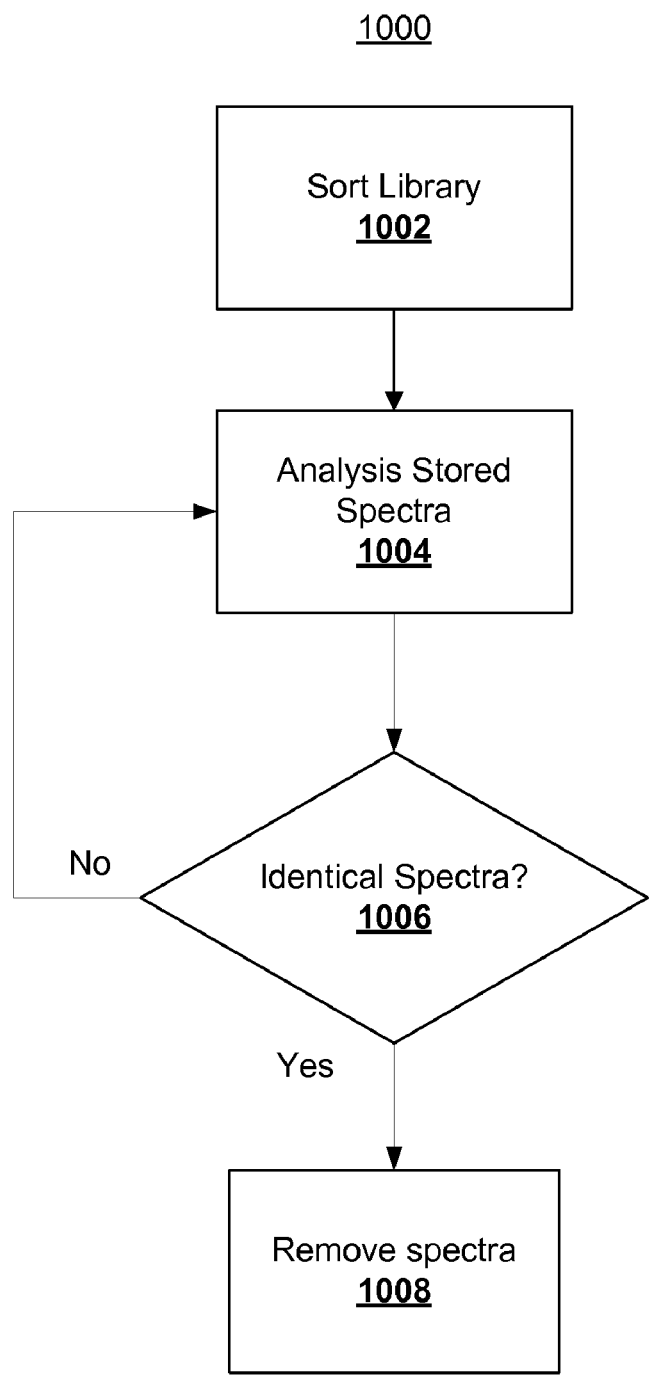
FIG. 10 illustrates an exemplary verification process for data stored in a library.

Optionally, the spectra collected can be verified to enhance the reliability of the library. FIG. 10 illustrates an exemplary verification process 1000 for the library. Referring to FIG. 10, the library is sorted (step 1000). This operation functions to expedite the verification process of the data stored in the library. If desired, this operation can be bypassed if the library contains less than a predetermined number of data. Once the library is sorted, spectra (and/or other wafer parameters) stored in the library are analyzed (step 1004). If it is determined that two or more spectra stored in the library are substantially identical yet exhibit a different thickness (step 1006), then both spectra are permanently discarded from the library ("Yes" branch of step 1008). Otherwise ("No" branch of step 1008), the analysis step is resumed.

In some implementations, spectra stored in the library are normalized, averaged and/or filtered to enhance the reliability of the library. For example, spectra matching can be performed after processing and filtering the measured spectra (e.g., using high pass filter or low pass filter) to remove noise and interference. The spectra also can be compensated for optical system distortions and other artifacts, or be matched to different optical response used to collect the spectra for the library. This may include, for example, intensity variations and wavelength dependent scattering due to the feature structure, array dimensions, numerical aperture effects, wavelength range and polarization.

In some implementations, each measured raw spectra can be normalized to remove light reflections contributed by mediums other than the film or films of interest. Normalization of spectra facilitates the comparison process discussed above. Light reflections contributed by media other than the film or films of interest include light reflections from, for example, the polishing transparent window 36 and from the base silicon layer of the wafer. Contributions from, for example, a transparent window 36 can be estimated by measuring the spectrum of light received by the in situ optical monitoring system 40 under a dark condition (i.e., when no wafers are placed over the in situ optical monitoring system 40). Contributions from, for example, the silicon layer can be estimated by measuring the spectrum of light reflecting off a bare silicon wafer. The contributions can be obtained prior to commencement of the polishing step.

A measured raw spectrum can be normalized as follows:

normalized spectrum=($A$−Dark)/($Si$−Dark)

where A is the raw spectrum, Dark is the spectrum obtained under the dark condition, and Si is the spectrum obtained from the bare silicon wafer.

Optionally, the collected spectra can be sorted based on the region of the pattern that has generated the spectrum, and spectra from some regions can be excluded from the endpoint calculation. In particular, spectra that are from light reflecting off scribe lines can be removed from consideration. Different regions of a reference wafer usually yield different spectra (even when the spectra were obtained at a same point of time during polishing).

For example, a spectrum of the light reflecting off a scribe line in a wafer can be different from the spectrum of the light reflecting off an array of the wafer. Because of their different shapes, use of spectra from both regions of the pattern usually introduces error into the endpoint determination. However, the spectra can be sorted based on their shapes into a group for scribe lines and a group for arrays. Because there is often greater variation in the spectra for scribe lines, usually these spectra can be excluded from consideration to enhance precision.

A high pass filter also can be applied to the measured raw spectra. Application of the high pass filter can remove low frequency distortion of the average of the subset of spectra. The high pass filter can be applied to the raw spectra, their average, or to both the raw spectra and their average.

In some implementations, based on the current spectra of each zone and the variations thereof, the computing device 48 can determine the flatness of the wafer and the polishing uniformity for CMP tool and process qualification. For example, the computing device 48 can applies process control and endpoint detection logic to determine when to change process and polish parameter and to detect the polishing endpoint. Possible process control and endpoint criteria for the detector logic include local minima or maxima, changes in slope, threshold values in amplitude or slope, or combinations thereof. The spectra of light reflected from a wafer can be frequently monitored and collected as polishing progresses. Based on the reflected spectra, the computing device 48 can determine an endpoint of a polishing process.

If more than one current spectra is measured for a platen revolution, then the spectra can be grouped, combined, e.g., averaged within each group, and the averages are designated to be current spectra. The spectra can be grouped by radial distance from the center of the wafer. By way of example, for a given platen rotation, a first current spectrum can be obtained, e.g., by averaging, from spectra measured as points 211 and 219 (FIG. 3), a second current spectrum can be obtained from spectra measured at points 212 and 218, a third current spectra can be obtained from spectra measured at points 213 and 217, and so forth.

Figure 11:
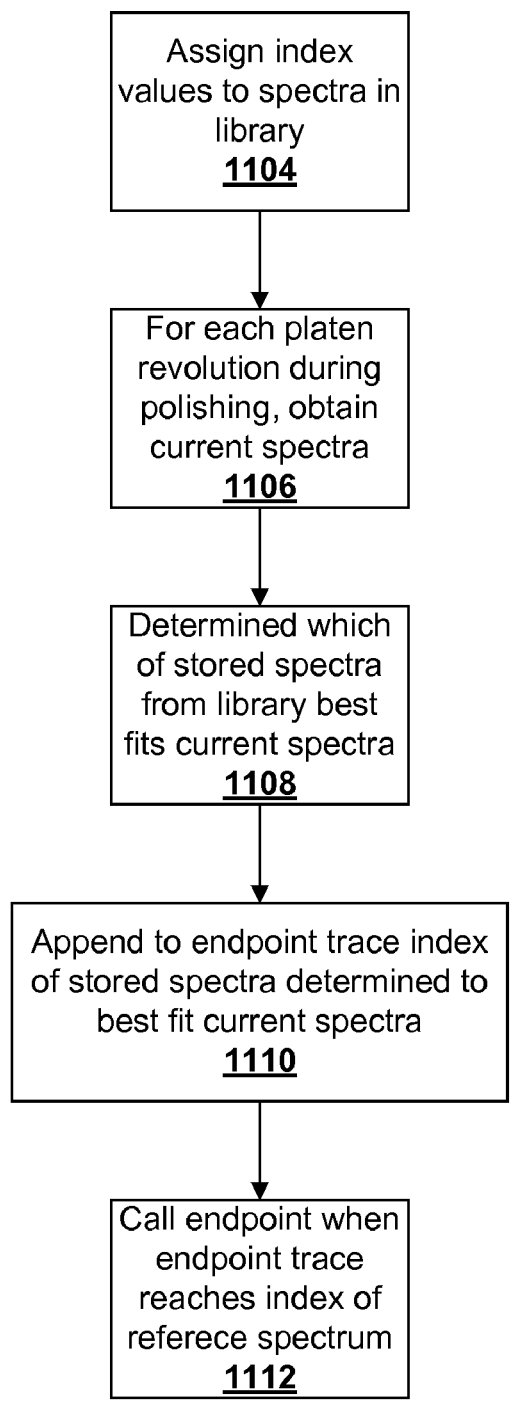
FIG. 11 shows a method for using spectrum based endpoint determination to determine an endpoint of a polishing step.

FIG. 11 shows another method 1100 for determining an endpoint of a polishing step. Initially, index values are assigned to the spectra in the library (step 1104). The index values can be selected to monotonically increase as polishing progresses, e.g., an index values can be proportional to a number of platen rotations. Thus, each index number can be a whole number, and the index number can represent the expected platen rotation at which the associated spectrum would appear. The library can be implemented in memory of the computing device of the polishing apparatus.

A wafer from the batch of wafers is polished, and the following steps are performed for each platen revolution. One or more spectra are measured to obtain a current spectra for a current platen revolution (step 1106). The spectra are obtained as described above. The spectra stored in the library which best fits the current spectra is determined (step 1108). The index of the library spectrum determined to best fits the current spectra is appended to an endpoint index trace (step 1110). Endpoint is called when the endpoint trace reaches a reference index, e.g., the index of a spectrum having the desired thickness or other substrate characteristic (step 1112).

Although implementations for determining a film thickness have been described, other parameters including shallow trench depth, step height of various semiconductor materials (e.g., silicon dioxide, silicon nitride), an area of trench or active region of the wafer, or thickness of silicon dioxide or pad layers.

Although the discussion above focuses on use of the library in a polishing endpoint detection system, the library could also be used in for an in-line spectrographic metrology system, e.g., an in-line system that scans a sensor across the substrate at relatively high speed. This in-line metrology system could be used before or after processing, e.g., polishing, of the substrate, and the substrate characteristics derived from the measured could be used for feed-forward or feed-back control of the polishing system. For example, if the library associates thicknesses with spectra, then the in-line metrology system could measure substrate layer thickness at multiple points along a radius or diameter of the substrate prior to polishing, and the measured layer thickness data could be used to control the polishing system (e.g., select endpoint criteria or polishing head pressures) during polishing of that substrate. As another example, the in-line metrology system could measure substrate layer thickness at multiple points along a radius or diameter of the substrate after polishing, and the measured layer thickness data could be used to control the polishing system (e.g., select endpoint criteria or polishing head pressures) during polishing of a subsequent substrate. Due to the large number of spectra stored in the system, the system can provide reliable measurements of the substrate characteristics without precise positioning of the sensor to any well-defined point, thereby permitting the measurements to be made at the in-line station at high throughput.

Figure 12:
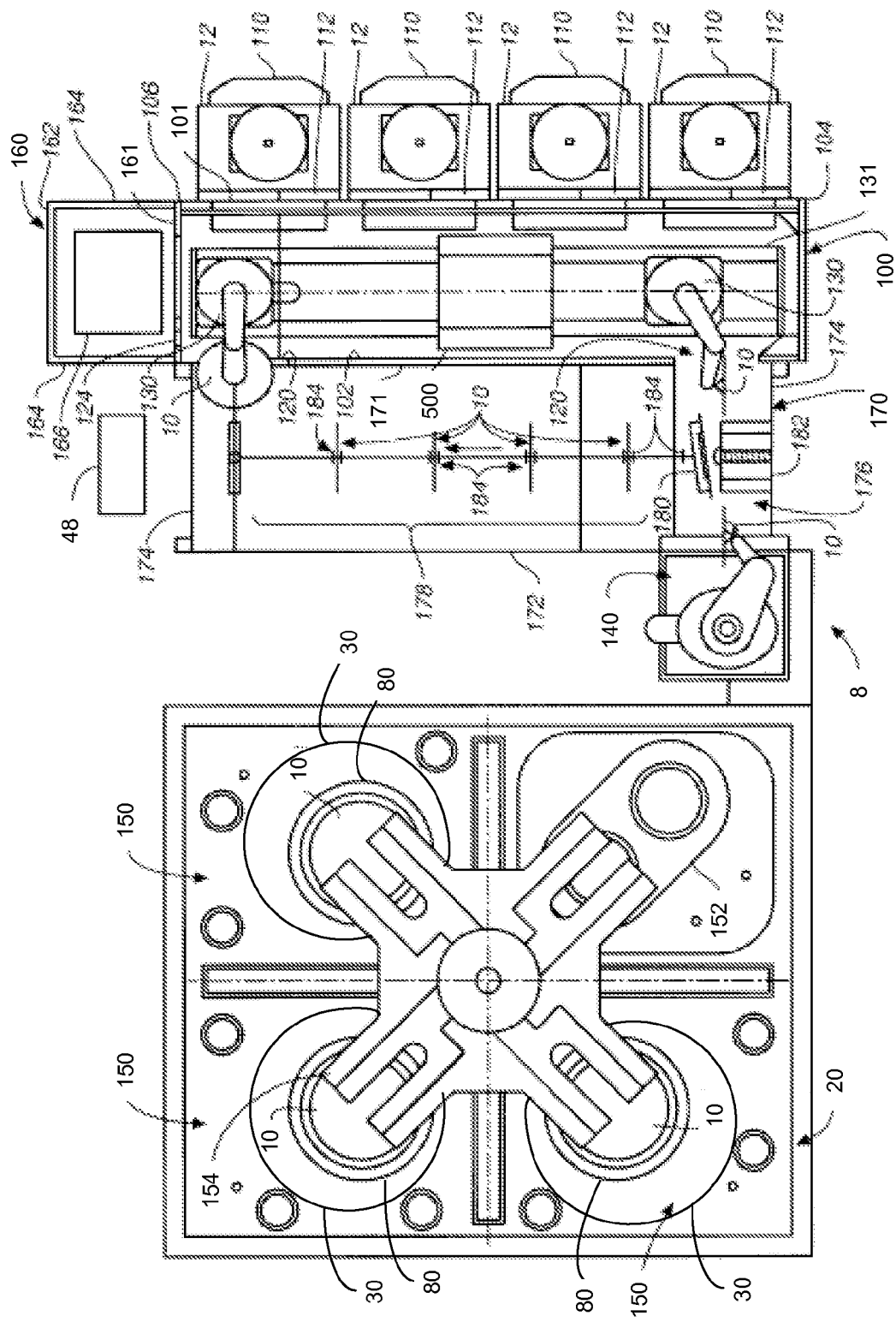
FIG. 12 is a top view of an exemplary substrate processing system having an in-line spectrographic monitoring system.

An implementation of a substrate processing system 8 that includes an in-line spectrographic metrology system 500 is illustrated in FIG. 12. The substrate processing system 8 includes the chemical mechanical polishing apparatus 20, a factory interface module 100, a wet robot 140, and a cleaner 170. Substrates 10, e.g., silicon wafers with one or more layers deposited thereon, are transported to the substrate processing system 8 in cassettes 12, and are extracted from the cassettes 12 by the factory interface module 100 for transport to the polishing apparatus 20 and the cleaner 170. The operations of the substrate processing system 8 are coordinated by controller 48, such as one or more programmable digital computers executing control software. Some of the modules, such as the wet robot 140 and cleaner 170, could be omitted, depending on the configuration of the processing system, and the processing system could include other modules, such as a deposition or etching apparatus.

The polishing apparatus 20 can includes a series of polishing stations 150 and a transfer station 152. The transfer station 152 serves multiple functions, including receiving individual substrates 10 from the wet robot 140, washing the substrates and loading the substrates into carrier heads. Each polishing station can includes a rotatable platen holding a polishing pad 30. Different polishing pads can be used at different polishing stations. A rotatable carousel 154 that holds four carrier heads 80 is supported above the polishing stations (drive systems above the carrier heads and the carrier head over the transfer station are not illustrated in FIG. 12 to provide a clearer top view). The carousel 154 rotates to carry the substrates between the polishing stations 150 and the transfer station 152.

The cleaner 170 can be generally rectangular shaped cabinet with a front wall 171, a back wall 172, and two side walls 174. The interior of the cleaner 170 is divided into an input or staging section 176 and a cleaning section 178. The staging section 176 includes a substrate-pass through support 180 and an indexable buffer 182, each of which can hold one or more substrates in a vertical orientation. The cleaner also includes a walking beam 184 which can hold a substrate in a vertical orientation.

The wet robot 140 is configured to transport the substrate between the staging section 176 and the polishing apparatus 20.

The factory interface module 100 can be substantially rectangular in shape and include an outer wall 101, an inner wall 102, a first side wall 104, and a second side wall 106. The outer wall 101 can be aligned with a cleanroom wall. A plurality (e.g., four) cassette support plates 110 project from the outer wall 101 into the cleanroom to accept the cassettes 12, and a plurality of cassette ports 112 are formed in the outer wall 101 to permit transport of the substrates from the cassettes 12 into the factory interface module 100. The inner wall 104 mates against a front wall 171 of the cleaner 170 and shares an entry port 120 (to the staging section 176) and an exit port 122 (from the end of the cleaning section 178) with the cleaner front wall 171. The inner wall 102 and the cleaner front wall 170 may be combined into one structure, and there may be additional ports from the factory interface module 100 to the cleaner 170.

Figure 13:
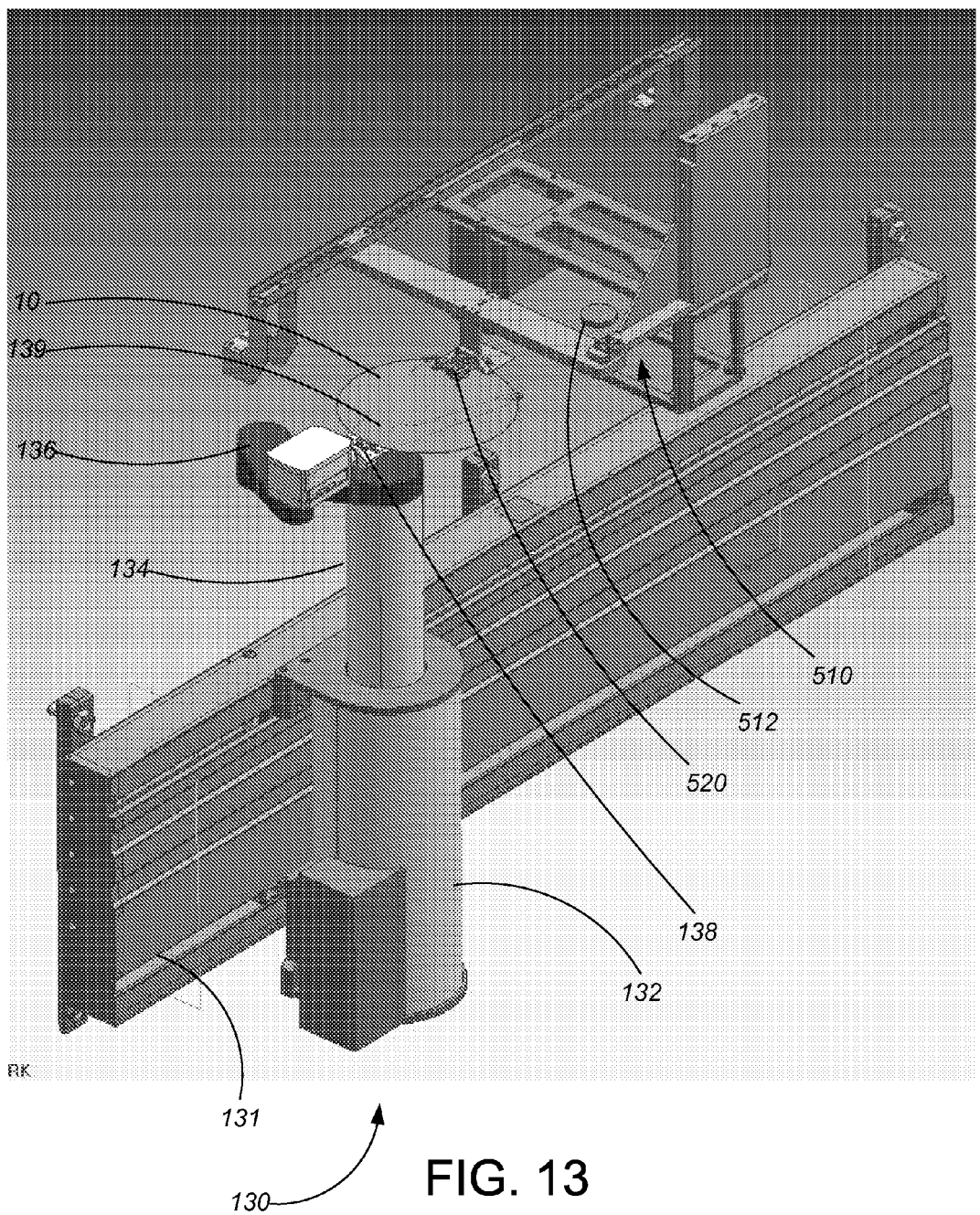
FIG. 13 is a perspective view of an interior of an exemplary factory interface module.
Figure 14:
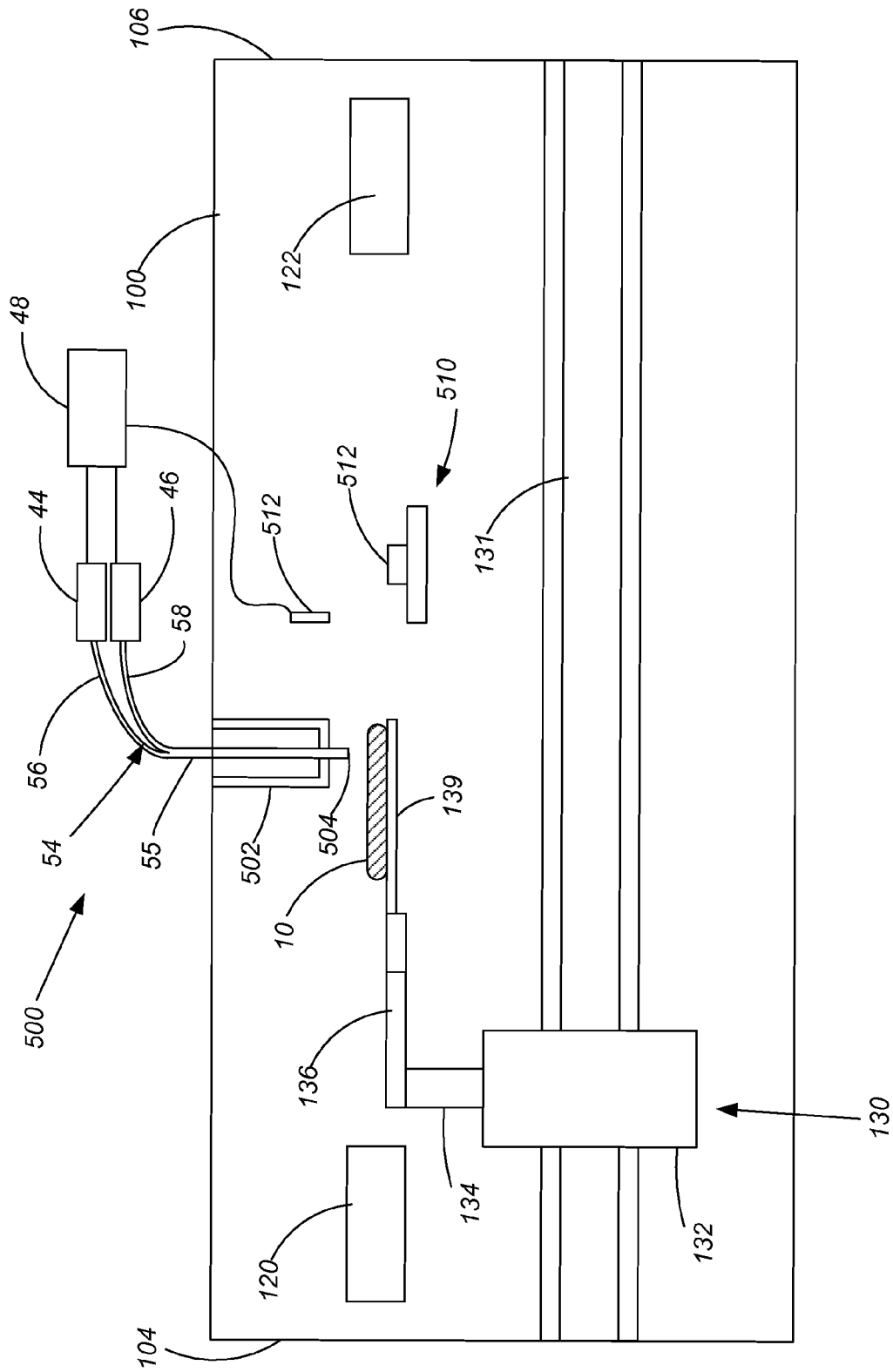
FIG. 14 is a side view of an exemplary factory interface module having an in-line spectrographic monitoring system.

One or more factory interface wafer handlers 130 (hereinafter simply "robot"), depicted in greater detail in FIGS. 13 and 14, are housed within the factory interface module 100. In some implementations the factory interface robot 130 has a base 132, a rotatable vertical shaft 134 extending from the base 132, a horizontally extendible articulated arm 136 supported by the shaft 134, a rotary actuator 138 at the end of the articulated arm 136, and a substrate gripper 139 (in phantom below the substrate 10 in FIG. 13) supported by the rotary actuator 138. The vertical shaft 134 is capable of lifting and lowering the articulated arm 136 vertically. Rotation of the vertical shaft 134 permits rotary motion of the articulated arm 136 about a vertical axis, and the articulated arm 136 is configured to extend and retract horizontally. The rotary actuator can be pivotally connected to the end of the articulated arm 136 so as to be rotatable about a vertical axis. In addition, the rotary actuator 138 can rotate the substrate gripper 139 about a horizontal axis. The factory interface robot 130 thus provides a wide range of motion to manipulate the substrate held by the gripper 139. The gripper 139 can be a vacuum chuck, an electrostatic chuck, an edge clamp, or similar wafer gripping mechanism. The factory interface robot can also include an optical detector to sense whether a substrate is being held by the gripper 140. Sensors, e.g., encoders, can be used to detect the position of the movable elements of the robot 130 so that the position of the gripper 139 and substrate 10 can be calculated.

The base 132 can be supported on a linear rail 131 that extends parallel to the inner and outer walls 102, 100. A motor can drive the factory interface robot 130 laterally along the rail 131 to access the entry port 120, the exit port 122, the cassette ports 112 (FIG. 12 illustrates two positions along the slide 142 for the factory interface robot 130), and the in-line spectrographic metrology system 500 within the factory interface 100.

As shown in FIG. 14, the in-line spectrographic monitoring system 500 operates similarly to the in-situ optical monitoring system, and includes a light source 44 and a light detector 46. Light passes from the light source 44, through an optical guide, impinges and is reflected from a substrate 10 held in the factory interface 100, back through the optical guide, and travels to the light detector 46. As with the in-situ system, a bifurcated optical cable 54 can be used to transmit the light from the light source 44 to the substrate 10 and back from the substrate 10 to the light detector 46. The bifurcated optical cable 54 can include a "trunk" 55 with an end 504 fixed in a position selected to be in proximity to substrate when the substrate is to be scanned by the metrology system, and two "branches" 56 and 58 connected to the light source 44 and light detector 46, respectively. The light source 44 and light detector 46 are connected to a computing device 48 that performs the various computational steps in the metrology process. Although FIG. 14 illustrates the light source 44 and a light detector 46 as positioned outside the factory interface 100, these components could be located inside the factory interface 100.

A bracket 502 secured to a wall of the factory interface 100 can hold the trunk 55 of the optical fiber 54 in a fixed position inside the factory interface 100. The robot 130 can be controlled to sweep the substrate at a working distance of two to thirty-five millimeters from the end 504 of the optical fiber.

The factory interface 100 can also include a pre-aligner 510 to position the substrate in a known rotational position. The pre-aligner 510 includes a rotatable support 512, such as a pedestal, possibly with a vacuum or electrostatic chuck, an edge support ring, or support pins, onto which the substrate can be placed. In addition, the pre-aligner 510 includes a notch detection system, such as an optical interrupter sensor 520, to sense when the substrate notch is at a specific angular position. During creation of a library, the reference substrate is placed by the robot 130 on the support 512, the support 512 rotates so that the sensor 520 detects the substrate notch, and rotates to place the substrate notch in a predetermined angular orientation. Then the robot 130 retrieves the substrate from the support 512. Thus, substrates which might be in an uncertain angular position, e.g., after a polishing operation, have a known orientation when scanned by the in-line spectrographic monitoring system 500, thus permitting accurate determination of the x-y (or r–θ) position of the measurements on the substrate. Because the position of the spectra measurements is known with higher accuracy, the reliability of the association of spectra measurements with substrate characteristics is improved.

The substrate processing system 8 can operate in two modes: an initial library creation mode and a later in-line monitoring mode. In the library creation mode the substrate processing system can generate a library for a particular type of substrate, e.g., a particular pattern and a particular metal or dielectric level in the fabrication process. In general, a separate library is created for each different metal or dielectric level in the fabrication process for each different pattern. In the in-line monitoring mode, the substrate processing system 8 uses the previously generated library to perform quickly determine the characteristics of substrates undergoing processing based on the measured spectrographic data.

Library generation occurs generally as discussed above with respect to FIG. 3. A reference substrate with a particular pattern and at a particular point in the fabrication process is measured using a conventional metrology system that provides very precise positioning of a sensor to well-defined locations on the substrate, e.g., a Nova or Nanometrics optical metrology system. The measurements can be made before or after a polishing step in the fabrication process. At least one characteristic of a reference substrate, e.g., layer thickness, is measured at multiple well-defined locations on the reference substrate, and the measured characteristic and the measurement location are stored, e.g., in a first data structure. The metrology system can be an in-line system within the processing system 8, or a stand alone system. However, one potential advantage of using the in-line spectrographic monitoring system described herein is that the processing system 8 need not include the conventional metrology system. In particular, because the conventional metrology system is needed only for accurate substrate characteristic measurements during library generation (rather than during production), a single stand alone metrology system should be able provide the necessary measurements for library generation for multiple processing systems 8.

The reference substrate 10a is placed into a cassette 112 and extracted from the cassette into the factory interface by the robot 130. The robot 130 moves the reference substrate to engage the pre-aligner so that the position of the substrate can be precisely identified. Then the reference substrate is held by the robot and moved past the optical probe. A sequence of spectrographic measurements are generated using the in-line metrology system 500, the position of each spectrographic measurement on substrate is determined, and the spectra and measurement locations are stored, e.g., in a second data structure.

Figure 15:
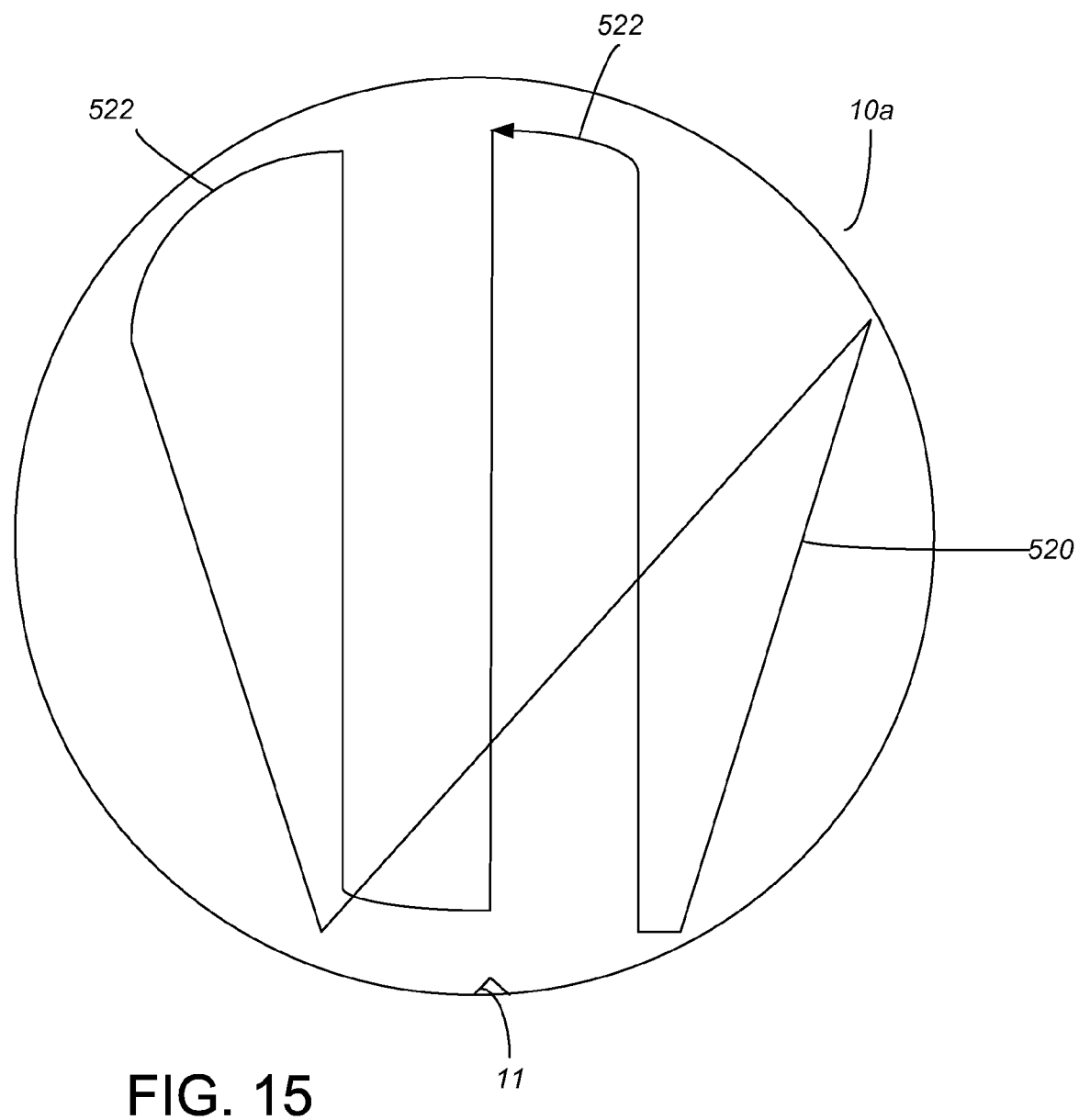
FIG. 15 illustrates an exemplary path of an optical probe of the in-line spectrographic monitoring system across a reference substrate during spectrographic measurements for library generation.

For gathering of spectrographic data for library generation, an exemplary path 520 of the optical probe 504 across a reference substrate 10a having a notch 11 is illustrated in FIG. 15. The path 520 can include several arcs 522 that pass along the substrate edge, e.g., within 8 mm, e.g., within 5 mm, of the substrate edge, to ensure that a significant number of measurements are obtained near the substrate edge.

Once both spectrographic data and characteristic measurements at well-defined locations are obtained, the library can then be generated by associating each spectrographic measurement from the first data structure with a characteristic measurement from the first data structure at a nearby well-defined location. The spectra can be measured at different locations on the reference substrate 10 by the in-line spectrographic monitoring system 500 before or after the substrate characteristic is measured by the metrology system.

Returning to FIGS. 13 and 14, during processing of device substrates, e.g., in a normal polishing operation, an unpolished substrate is retrieved by the factory interface robot 130 from one of the cassettes 112. The factory interface robot 130 "picks" the substrate, e.g., by vacuum suction, and transports the unpolished substrate at relatively high speed past the optical probe of the in-line spectrographic monitoring system 500 in the factory interface. Thus, the robot 130 acts as the stage to hold the substrate during the measurement process. The in-line spectrographic monitoring system 500 measures spectra for a sequence of points across the substrate as the substrate is scanned, and a layer thickness measurement is generated for at least some of the measured points. These pre-polish layer thickness measurements can be used to adjust the polishing process parameters for the substrate.

The robot 130 then transports the substrate through the entry port 120 to the staging section 176. There, the substrate is placed in either the pass-through support 180 or the indexible buffer 182. The wet robot 140 then extracts the substrate 10 from the staging section 176 and places the substrate 10 into the transfer station 152 of the polishing apparatus 20. From the transfer station 152, the substrate 10 is carried to one or more polishing stations 150 to undergo chemical mechanical polishing. After polishing, the wet robot 140 transports the substrate 10 from the transfer station 152 to the walking beam 184 in the cleaner 120. The walking beam 184 transports the substrate through the cleaner section 178 of the cleaner 120. While the substrate 10 is transported through the cleaner section 178, slurry and other contaminants that have accumulated on substrate surface during polishing are removed.

The factory interface robot 130 removes the substrate 10 from the cleaner 120 through the exit port 122, and transports the polished substrate at relatively high speed past the optical probe of the in-line spectrographic monitoring system 500 in the factory interface 100. Again, the in-line spectrographic monitoring system 500 measures spectra for a sequence of points across the substrate as the substrate is scanned, and a layer thickness measurement is generated for at least some of the measured points. These post-polish layer thickness measurements can be used to adjust the polishing process parameters for a subsequent substrate. Finally, the factory interface robot 130 returns the substrate 10 to one of the cassettes 112.

Figure 16:
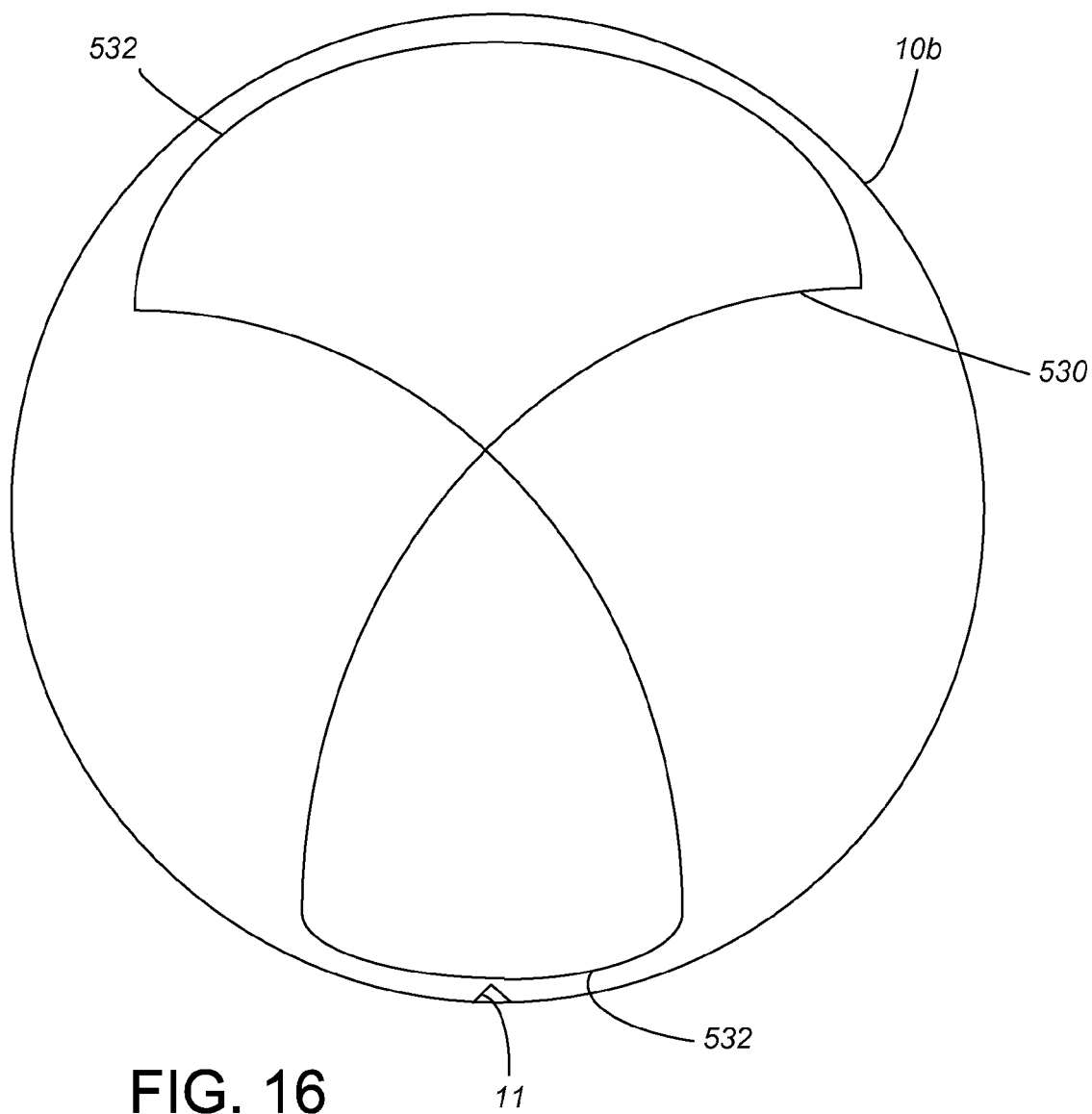
FIG. 16 illustrates an exemplary path of an optical probe of the in-line spectrographic monitoring system across a device substrate during spectrographic measurements for data collection for processing control.

For gathering of spectrographic data during device substrate processing for control of polishing parameters, an exemplary path 530 of the optical probe 504 across a device substrate 10b having a notch 11 is illustrated in FIG. 16. In some implementations, the path 530 describes a "figure eight" shape on the substrate. The path 530 can include several arcs 532 that pass along the substrate edge, e.g., within 8 mm, e.g., within 5 mm, of the substrate edge, to ensure that a significant number of measurements are obtained near the substrate edge.

The robot 130 can move the substrate at a fairly high speed across the substrate. For example, the robot could move a 300 mm diameter substrate to cause the optical probe to trace the path shown in FIG. 16 in about three to seven seconds, e.g., about six seconds. The detector 46 can have a sampling rate of about 130 to 150 samples per second, e.g., 142 samples per second (the light source 44 can flash on for each spectrographic measurement). Thus, assuming that path 530 is traced over about 6 seconds, about 850 spectra can be measured along the path. Due to the high speed of the in-line measurement, e.g., a velocity of about 150-350 mm/sec during many measurements, during production each and every substrate can undergo both pre-polish and post-polish measurement without impacting substrate throughput (for throughput <85 wafer per hour). Thus, for each substrate, thickness measurements at a variety of radial positions on the substrate can be used to control processing conditions for that substrate or for a subsequent substrate.

Optionally, the in-line spectrographic metrology system could be housed in a separate module 160 connected to the factory interface module 100. For example, one of the side walls 104 or 106 (side wall 106 in the implementation shown in FIG. 12) mates with a wall 161 of the metrology module 160 and shares an access port 124. The side wall 104 and the monitoring system wall 161 may be combined into one structure, and there may be additional ports from the factory interface module 100 to the metrology module 160. The metrology module 160 could include a separate robot for the substrate, or the factory interface robot 130 could manipulate the substrate, to cause the substrate to be scanned past the spectrographic probe.

The subject matter described herein contemplates a comprehensive thin-film metrology and polishing system, which combines measurements of patterned wafers irrespective of locations of the measurements. It offers both real-time, in-line measurements (i.e. performed within a semiconductor fabrication tool) and also rapid multi-point (i.e. mapping) at-line measurements of film thickness, composition, and electronic properties. The present concepts can be applied broadly to many of the critical electronic materials that are processed in semiconductor fabrication tools, including polysilicon, silicon dioxide, silicon nitride, and other dielectrics.

Implementations and all of the functional operations described in this specification can be implemented in digital electronic circuitry, or in computer software, firmware, or hardware, including the structural means disclosed in this specification and structural equivalents thereof, or in combinations of them. Implementations described herein can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple processors or computers. A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

The above described polishing apparatus and methods can be applied in a variety of polishing systems. Either the polishing pad, or the carrier head, or both can move to provide relative motion between the polishing surface and the wafer. For example, the platen may orbit rather than rotate. The polishing pad can be a circular (or some other shape) pad secured to the platen. Some aspects of the endpoint detection system may be applicable to linear polishing systems (e.g., where the polishing pad is a continuous or a reel-to-reel belt that moves linearly). The polishing layer can be a standard (for example, polyurethane with or without fillers) polishing material, a soft material, or a fixed-abrasive material. Terms of relative positioning are used; it should be understood that the polishing surface and wafer can be held in a vertical orientation or some other orientations.

Particular implementations have been described. Other implementations are within the scope of the following claims. For example, the actions recited in the claims can be performed in a different order and still achieve desirable results.

What is claimed is:

1. A method of generating a library from a reference substrate for use in processing a product substrate other than the reference substrate, the method comprising:
   measuring substrate characteristics at a plurality of well-defined points of a reference substrate with a first metrology system;
   measuring spectra at a plurality of measurement points of the reference substrate with a second monitoring system other than the first metrology system to generate a plurality of measured spectra, the plurality of measurement points including points other than the well-defined points and the plurality of well-defined points including points other than the measurement points, there being more measurement points than well-defined points;
   for each measured spectrum of the plurality of measured spectra, determining in a processor at least one well-defined point from the plurality of well-defined points that is proximate to a measurement point of the measured spectrum;
   after measuring the substrate characteristics and measuring the spectra, for each measured spectrum of the plurality of measured spectra, in a processor, calculating a substrate characteristic based on a measured substrate characteristics of the proximate well-defined point; and
   for each measured spectrum of the plurality of measured spectra, storing in a memory the measured spectrum, the calculated substrate characteristic and an association of the calculated substrate characteristic with the measured spectrum to generate the library for use in processing a product substrate other than the reference substrate.

2. The method of claim 1, further comprising:
   storing coordinates of the well-defined points; and
   storing coordinates of the measurement points.

3. The method of claim 2, wherein determining at least one well-defined point that is proximate the measurement point comprises comparing coordinates of at least some of the well-defined points with coordinates of the measurement point.

4. The method of claim 3, wherein comparing coordinates of the well-defined points with coordinates of the measurement point includes determining distances between the measurement point and the at least some of the well-defined points.

5. The method of claim 4, wherein determining at least one well-defined point that is proximate the measurement point comprises includes determining a well-defined point that is nearest to the measurement point.

6. The method of claim 1, wherein the substrate characteristic includes a layer thickness.

7. The method of claim 6, wherein the substrate characteristic include a pre- or post-polish layer thickness.

8. The method of claim 6, further comprising:
   removing identical spectra exhibiting different layer thickness values.

9. The method of claim 6, wherein the first metrology system comprises a contact profilometer.

10. The method of claim 1, wherein the substrate characteristic includes a layer conductivity.

11. The method of claim 10, wherein the first metrology system comprises a four-point probe.

12. The method of claim 1, where the plurality of well-defined points are at substantially similar relative locations within different dies on the reference substrate.

13. The method of claim 1, wherein at least some of the measurement points are spatially different than the well-defined points.

14. The method of claim 13, wherein substrate characteristics are measured prior to measuring the spectra.

15. The method of claim 13, wherein substrate characteristics are measured after measuring the spectra.

16. The method of claim 1, wherein measuring the spectra comprises scanning a sensor across the reference substrate.

17. The method of claim 16, wherein the spectra are measured while the reference substrate is moving relative to an optical probe.

18. The method of claim 1, wherein measuring substrate characteristics is performed at a stand-alone metrology system.

19. The method of claim 18, wherein measuring spectra is performed at an in-line optical monitoring system of a substrate processing system.

20. A method of monitoring a product substrate, comprising:
generating the library from the reference substrate according to the method of claim 1;
scanning the product substrate other than the reference substrate with a optical monitoring system to generate a plurality of spectra; and
determining substrate characteristics for the product substrate based on the library.

21. The method of claim 20, wherein scanning the product substrate comprises scanning with an in-situ monitoring system.

22. The method of claim 20, wherein scanning the product substrate comprises scanning with an in-line monitoring system.

23. A computer program product, tangibly stored on machine readable storage device, the product comprising instructions operable to cause a processor to:

cause substrate characteristics to be measured at a plurality of well-defined points of a reference substrate with a first metrology system;
cause spectra to be measured at a plurality of measurement points of the reference substrate with a second monitoring system other than the first metrology system to generate a plurality of measured spectra, the plurality of measurement points including points other than the well-defined points and the plurality of well-defined points including points other than the measurement points, there being more measurement points than well-defined points;
for each measured spectrum of the plurality of measured spectra, determine at least one well-defined point from the plurality of well-defined points that is proximate to a measurement point of the measured spectrum;
after measuring the substrate characteristics and measuring the spectra, for each measured spectrum of the plurality of measured spectra calculating a substrate characteristic based on a measured substrate characteristic of the proximate well-defined point; and
for each measured spectrum of the plurality of measured spectra, storing an association of the calculated substrate characteristic with the measured spectrum.

* * * * *